United States Patent
Mao et al.

(10) Patent No.: US 6,376,644 B1
(45) Date of Patent: *Apr. 23, 2002

(54) BIODEGRADABLE POLYMERS CHAIN-EXTENDED BY PHOSPHATES, COMPOSITIONS, ARTICLES AND METHODS FOR MAKING AND USING THE SAME

(75) Inventors: Hai-Quan Mao, Towson; Kam W. Leong, Ellicott City; Zhong Zhao, Baltimore, all of MD (US); James P. English, Chelsea, AL (US)

(73) Assignees: Guilford Pharmaceuticals, Inc.; Johns Hopkins University School of Medicine, both of Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/654,326

(22) Filed: Sep. 1, 2000

Related U.S. Application Data

(63) Continuation of application No. 09/053,649, filed on Apr. 2, 1998, now Pat. No. 6,166,173, which is a continuation-in-part of application No. 08/832,217, filed on Apr. 3, 1997, now abandoned.

(51) Int. Cl.[7] ............... C08G 79/04; A61K 31/80
(52) U.S. Cl. ............ 528/398; 427/78.37; 427/426; 427/486; 523/111; 523/113; 525/538; 528/352; 528/400; 623/1; 623/12; 623/16 C
(58) Field of Search ................ 523/111, 113; 424/78.37, 426, 486; 528/352, 400, 398, 538; 623/1, 12, 16 C

(56) References Cited

U.S. PATENT DOCUMENTS

| | | | |
|---|---|---|---|
| 5,952,451 A | 9/1999 | Zhao | 528/272 |
| 6,008,318 A | 12/1999 | Zhao et al. | 528/398 |
| 6,166,173 A | * 12/2000 | Mao et al. | 528/398 |

FOREIGN PATENT DOCUMENTS

| WO | WO 97/40085 | 10/1997 |
|---|---|---|

OTHER PUBLICATIONS

Fu et al., "Studies on the Melt Copolymerization of Phoshorus–Containing Diacid and BIS (p–Carboxyphenoxy) Propand for DDS," J. Wuhan Univ. (Natural Science Edition), 43(4):467–470 (1997).

Fu et al., "Studies on the Syntheses and Drug Release Properties of Polyanhydrides Containing Phosphonoformic (or Acetic) Acid Ethyl Ester in the Main Chain," Chemical Journal of Chinese Universities, 18(10)1706–1710 (1997).

Fu et al., "Studies on the Syntheses and Properties of Phosphorus–Containing Polyanhydrides for DDS," Chemical Journal of Chinese Universities, 18(5):813–817 (1997).

Liu et al., "Synthesis of Phosphatidyl Ethanolamine Polyphosphate Liposomal Materials," Chemical Journal of Chinese Universities, 18(9):1556–1559 (1997).

Penczek et al., "Phosphorus–Containing Polymers," Handbook of Polymer Synthesis, Part B, Ch. 17, 1077–1132 (Dricheldorf ed. 1992).

Mao et al., "Design of New Biodegradable Polymers Based on Chain–Extension of Oligomeric Lactides by Phosphates," Proceedings of the Topical Conference on Biomaterials Carriers for Drug Delivery and Scaffold for Tissue Engineering, Peppas, N.A. et al., eds. Los Angeles, CA, pp. 193–195 (1997).

* cited by examiner

*Primary Examiner*—Peter Szekely
(74) *Attorney, Agent, or Firm*—Foley, Hoag & Eliot, LLP

(57) ABSTRACT

Biodegradable polymers are described comprising the recurring monomeric units shown in formula I or II:

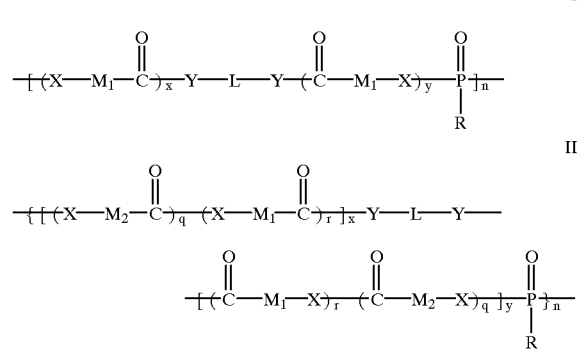

wherein X is —O— or —NR'—, where R' is H or alkyl; L is a branched or straight chain aliphatic group having from 1–20 carbon atoms; $M_1$ and $M_2$ are each independently (1) a branched or straight chain aliphatic group having from 1–20 carbon atoms; or (2) a branched or straight chain, oxy-, carboxy- or amino-aliphatic group having from 1–20 carbon atoms; Y is —O—, —S— or —NR'—, where R' is H or alkyl; R is H, alkyl, alkoxy, aryl, aryloxy, heterocyclic or heterocycloxy; the molar ratio of x:y is about 1; the molar ratio n:(x or y) is between about 200:1 and 1:200; and the molar ratio q:r is between about 1:99 and 99:1; wherein said biodegradable polymer is biocompatible before and upon biodegradat. Processes for preparing the polymers, compositions containing the polymers and biologically active substances, articles useful for implantation or injection into the body fabricated from the compositions, and methods for controllably releasing biologically active substances using the polymers, are also described.

116 Claims, 14 Drawing Sheets

P(LAEG-EOP), CHCl3, BB, 2/24/97
OBSERVE P31
 FREQUENCY 161.903 MHz
 SPECTRAL WIDTH 16000.0 Hz
 ACQUISITION TIME 0.800 sec
 RELAXATION DELAY 0.000 sec
 PULSE WIDTH 10.0 μsec
 AMBIENT TEMPERATURE
 NO. REPETITIONS 746
DECOUPLER H1
 HIGH POWER 33
 DECOUPLER CONTINUOUSLY ON
 WALTZ16 MODULATED
 DOUBLE PRECISION ACQUISITION
DATA PROCESSING
 LINE BROADENING 10.0 Hz
 FT SIZE 32768
 TOTAL ACQUISITION TIME 9 minutes

| Inflammatory Response at the Site of Implantation (i.m.) | | | | | | |
|---|---|---|---|---|---|---|
| Polymer | 3 D | 7 D | 14 D | 1 M | 2 M | 4 M |
| P(LAEG-EOP) | SI (130) | SI (123) | SI (180) | SI (198) | SI (106) | SI (99) |
| PLGA(RG755) | SI (148) | SI (98) | SI (137) | SI (105) | SI (94) | SI (43) |
| Score: | No Irritation (0) | Slight Irritation (0-200) | Mild Irritation (200-400) | Moderate Irritation (400-600) | Severe Irritation (>600) | |

FIG. 12

BIODEGRADABLE POLYMERS CHAIN-EXTENDED BY PHOSPHATES, COMPOSITIONS, ARTICLES AND METHODS FOR MAKING AND USING THE SAME

RELATED APPLICATIONS

This application is a continuation of U.S. Ser. No. 09/053,649, filed Apr. 2, 1998 now U.S. Pat. No. 6,166,173, the specification of which is hereby incorporated by reference in its entirety which is a CIP of Ser. No. 08/832,217, filed Apr. 3, 1997, abandoned.

BACKGROUND OF THE INVENTION

1. Field of the Invention

The present invention relates to biodegradable polymer compositions, in particular those containing both phosphate and ester linkages in the polymer backbone and that degrade in vivo into non-toxic residues. The polymers of the invention are particularly useful as implantable medical devices and drug delivery systems.

2. Description of the Prior Art

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more nearly maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., "Chemical and Physical Structures of Polymers as Carriers for Controlled Release of Bioactive Agents", *J. Macro Science, Rev. Macro. Chem. Phys.*, C23 (1), 61–126 (1983). As a result, less total drug is required, and toxic side effects can be minimized. Polymers have been used as carriers of therapeutic agents to effect a localized and sustained release. See Leong et al., "Polymeric Controlled Drug Delivery", *Advanced Drug Delivery Reviews*, 1:199–233 (1987); Langer et al., "New Methods of Drug Delivery", *Science*, 249:1527–33 (1990); and Chien et al., *Novel Drug Delivery Systems* (1982). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released. This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusional release, also allows controlled release of the therapeutic agent by degradation of the polymer matrix. Examples of classes of synthetic polymers that have been studied as possible biodegradable materials include polyesters (Pitt et al., "Biodegradable Drug Delivery Systems Based on Aliphatic Polyesters: Application to Contraceptives and Narcotic Antagonists", *Controlled Release of Bioactive Materials*, 19–44 (Richard Baker et al. ed. 1980)); poly(amino acids) and pseudo-poly(amino acids) (Pulapura et al., "Trends in the Development of Bioresorbable Polymers for Medical Applications", *Journal of Biomaterials Applications*, 6(1), 216–50 (1992)); polyurethanes (Bruin et al., "Biodegradable Lysine Diisocyanate-based Poly(glycolide-co-$\epsilon$-caprolactone)-urethane Network in Artificial Skin", *Biomaterials*, 11(4), 291–95 (1990)); polyorthoesters (Heller et al., "Release of Norethindrone from Poly(OrthoEsters)", *Polymer Engineering and Science*, 21(11), 727–31 (1981)); and polyanhydrides (Leong et al., "Polyanhydrides for Controlled Release of Bioactive Agents", *Biomaterials* 7(5), 364–71 (1986)). Specific examples of biodegradable materials that are used as medical implant materials are polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone).

Polymers having phosphate linkages, called poly(phosphates), poly(phosphonates) and poly(phosphites), are known. See Penczek et al., "Phosphorus-Containing Polymers", *Handbook of Polymer Synthesis, Part B*, Chapter 17, 1077–1132 (Hans R. Kricheldorf ed. 1992). The respective structures of these three classes of compounds, each having a different sidechain connected to the phosphorus atom, are as follows:

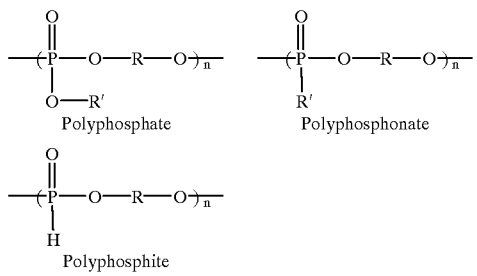

The versatility of these polymers comes from the versatility of the phosphorus atom, which is known for a multiplicity of reactions. Its bonding can involve the 3p orbitals or various 3s-3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable. Kadiyala et al., "Poly(phosphoesters): Synthesis, Physicochemical Characterization and Biological Response", *Biomedical Applications of Synthetic Biodegradable Polymers,* Chapter 3: 33–57 (Jeffrey O. Hollinger ed., 1995).

An additional feature of poly(phosphoesters) is the availability of functional side groups. Because phosphorus can be pentavalent, drug molecules or other biologically active substances can be chemically linked to the polymer. For example, drugs with —O-carboxy groups may be coupled to the phosphorus via an ester bond, which is hydrolyzable. The P—O—C group in the backbone also lowers the glass transition temperature of the polymer and, importantly, confers solubility in common organic solvents, which is desirable for easy characterization and processing.

Friedman, U.S. Pat. No. 3,442,982, discloses a poly (phosphoester-co-ester) polymer having, as its ester portion, the following asymmetric group:

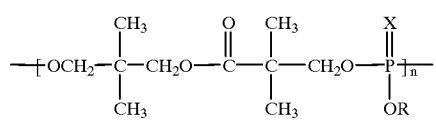

The polymers of Friedman are noted as being stable to hydrolysis, heat and light. (Column 1, lines 42–44 and column 3, lines 74–75).

Starck et al., Canadian Patent No. 597,473, disclose poly(phosphonates), and the incorporation of the phosphorus is said to make the resulting polymers incombustible. (Column 6, lines 1–2). Engelhardt et al., U.S. Pat. No. 5,530,093 discloses a multitude of textile finishing compositions having a wide variety of polycondensate structures with phosphoester and ester recurring units. The ester portions of Starck et al. and Engelhardt et al. are oriented as follows:

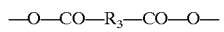

There remains a need for materials such as the poly (phosphoester-co-ester) compounds of the invention, which are particularly well-suited for making biodegradable materials and other biomedical applications.

SUMMARY OF THE INVENTION

The biodegradable polymers of the invention comprise the recurring monomeric units shown in formula I or II:

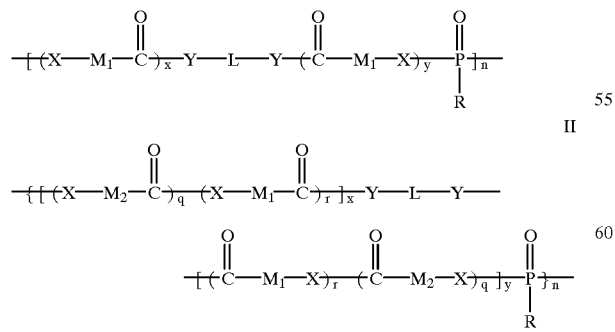

wherein

X is —O— or —NR'—, where R' is H or alkyl;

$M_1$ and $M_2$ are each independently (1) a branched or straight chain aliphatic group having from 1–20 carbon atoms; or (2) a branched or straight chain, oxy-, carboxy- or amino-aliphatic group having from 1–20 carbon atoms;

Y is —O—, —S— or —NR'—;

L is a branched or straight chain aliphatic group having from 1–20 carbon atoms;

R is H, alkyl, alkoxy, aryl, aryloxy, heterocyclic or heterocycloxy;

the molar ratio of x:y is about 1;

the molar ratio n:(x or y) is between about 200:1 and 1:200; and the molar ratio q:r is between about 1:99 and 99:1. These biodegradable polymers are biocompatible before and upon biodegradation.

In another embodiment, the invention comprises polymer compositions comprising:

(a) at least one biologically active substance and (b) a polymer having the recurring monomeric units shown in formula I or II.

In yet another embodiment of the invention, an article useful for implantation, injection, or otherwise being placed totally or partially within the body, comprises the biodegradable polymer of formula I or II or the above-described polymer compositions.

In a further embodiment, the invention contemplates a process for preparing a biodegradable polymer comprising the steps of:

(a) reacting a heterocyclic ring compound having formula III, IV, or V:

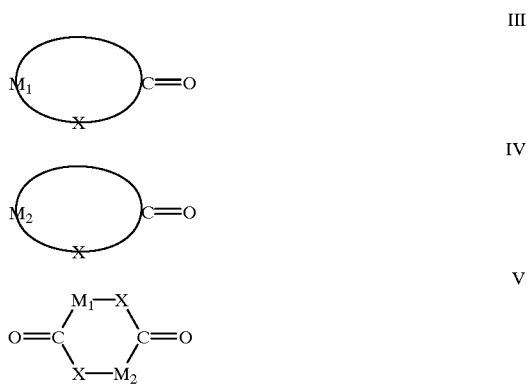

wherein $M_1$, $M_2$ and X are as defined above, with an initiator having the formula:

wherein Y and L are as defined as above, to form a prepolymer of formula VI or VII, shown below:

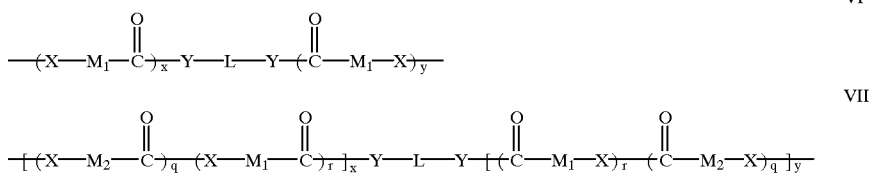

wherein X, $M_1$, $M_2$, Y, L, x, y, q and r are as defined above; and (b) further reacting said prepolymer of formula III, IV or V with a phosphorodihalidate of formula VIII:

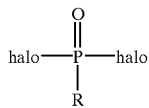

where "halo" is Br, Cl or I; and R is as defined above, to form said polymer of formula I or II.

In another embodiment of the invention, a method is provided for the controlled release of a biologically active substance comprising the steps of:

(a) combining the biologically active substance with a biodegradable polymer having the recurring monomeric units shown in formula I or II to form an admixture;

(b) forming the admixture into a shaped, solid article; and (c) implanting or injecting the solid article in vivo at a preselected site, such that the solid implanted or injected article is in at least partial contact with a biological fluid.

BRIEF DESCRIPTION OF THE DRAWINGS

FIG. 12 shows biocompatibility data for polymers of the invention.

DETAILED DESCRIPTION OF THE INVENTION

Polymers of the Invention

Figure 1:
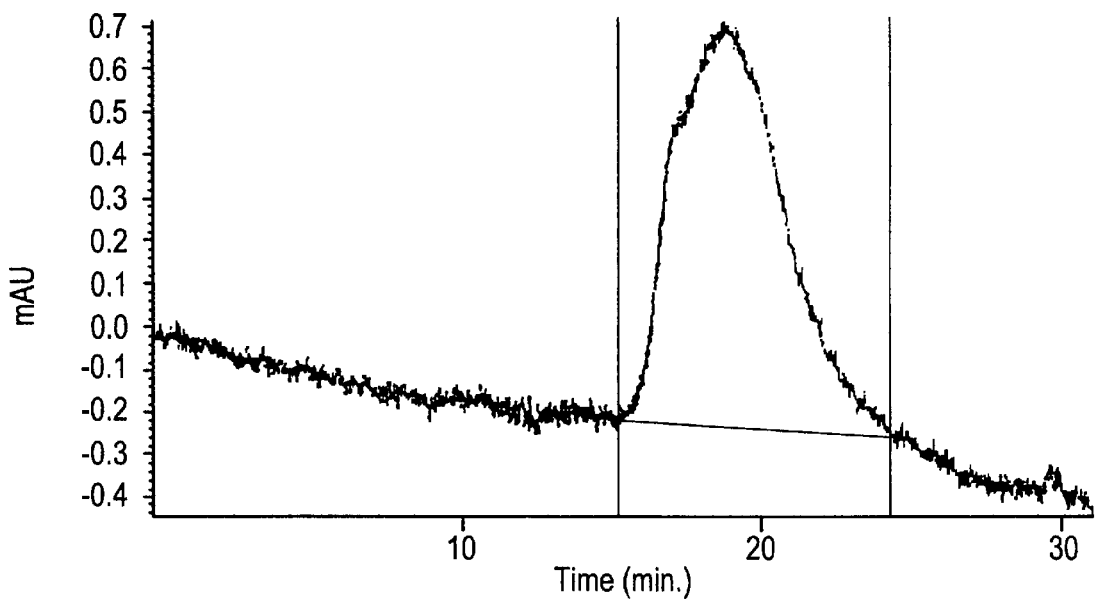
FIG. 1 shows the results of a GPC analysis of a polymer of the invention in graphic form.

As used herein, the term "aliphatic" refers to a linear, branched, cyclic alkane, alkene, or alkyne. Preferred aliphatic groups in the poly(phosphoester-co-ester) polymer of the invention are linear or branched and have from 1 to 10 carbons, preferably being linear groups having from 1 to 7 carbon atoms.

As used herein, the term "aryl" refers to an unsaturated cyclic carbon compound with 4n+2 π electrons.

As used herein, the term "heterocyclic" refers to a saturated or unsaturated ring compound having one or more atoms other than carbon in the ring, for example, nitrogen, oxygen or sulfur.

The biodegradable polymer of the invention comprises the recurring monomeric units shown in formula I or II:

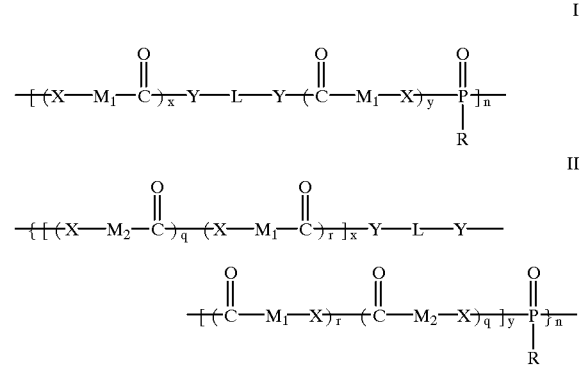

wherein X is —O— or —NR'— where R' is H or alkyl.

L can be any divalent branched or straight chain aliphatic group having from 1–20 carbon atoms, so long as it does not interfere with the polymerization or biodegradation reactions of the polymer. Specifically, L can be an alkylene group, such as methylene, ethylene, 1,2-dimethyl-ethylene, n-propylene, isopropylene, 2,2-dimethylpropylene or tert-butylene, n-pentylene, tert-pentylene, n-hexylene, n-heptylene and the like; an alkylene substituted with a non-interfering substituent, for example, hydroxy-, halogen- or nitrogen-substituted alkylene; an alkenylene group such as ethenylene, propenylene, 2-(3-propenyl)-dodecylene; and an alkynylene group such as ethynylene, proynylene, 1-(4-butynyl)-3-methyldecylene; and the like.

Preferably, however, L is independently a branched or straight chain alkylene group, more preferably, an alkylene group having from 1 to 7 carbon atoms. Even more preferably, L is an ethylene group or a methyl-substituted methylene group and, most preferably L is an ethylene group.

$M_1$ and $M_2$ in the formula are each independently either (1) a branched or straight chain aliphatic group having from 1–20 carbon atoms or (2) a branched or straight chain, oxy-, carboxy- or amino-aliphatic group having from 1–20 carbon atoms. In either case the branched or straight chain aliphatic group can be any divalent aliphatic moiety having from 1–20 carbon atoms, preferably 1–7 carbon atoms, that does not interfere with the polymerization, copolymerization or biodegradation reactions of the polymers. Specifically, when either $M_1$ or $M_2$ is a branched or straight chain aliphatic group having from 1–20 carbon atoms, it can be, for example, an alkylene group, such as methylene, ethylene, 1-methylethylene, 1,2-dimethylethylene, n-propylene, trimethylene, isopropylene, 2,2-dimethylpropylene, tert-butylene, n-pentylene, tert-pentylene, n-hexylene, n-heptylene, n-octylene, n-nonylene, n-decylene, n-undecylene, n-dodecylene, and the like; an alkenylene group, such as n-propenylene, 2-vinylpropylene, n-butenylene, 3-ethenylbutylene, n-pentenylene, 4-(3-propenyl)hexylene, n-octenylene, 1-(4-butenyl)-3-methyldecylene, 2-(3-propenyl)dodecylene, hexadecenylene and the like; an alkynylene group, such as ethynylene, propynylene, 3-(2-ethynyl)pentylene, n-hexynylene, 2-(2-propynyl)decylene, and the like; or an alkylene, alkenylene or alkynylene group substituted with a non-interfering substituent, for example, a hydroxy, halogen or nitrogen group, such as 2-chloro-n-decylene, 1-hydroxy-3-ethenylbutylene, 2-propyl-6-nitro-10-dodecynylene, and the like.

When either $M_1$ or $M_2$ is a branched or straight chain, oxy-aliphatic group having from 1–20 carbon atoms, it can be, for example, a divalent alkoxylene group, such as ethoxylene, 2-methylethoxylene, propoxylene, butoxylene, pentoxylene, dodecyloxylene, hexadecyloxylene, and the like. When $M_1$ or $M_2$ is a branched or straight chain, oxy-aliphatic group, preferably, it has the formula —O—$(CH_2)_a$— where a is 1 to 7.

When either $M_1$ or $M_2$ is a branched or straight chain, oxy-aliphatic group having from 1–20 carbon atoms, it can also be, for example, a dioxyalkylene group such as dioxymethylene, dioxyethylene, 1,3-dioxypropylene, 2-methoxy-1,3-dioxypropylene, 1,3-dioxy-2-methylpropylene, dioxy-n-pentylene, dioxy-n-octadecylene, methoxylene-methoxylene, ethoxylene-methoxylene, ethoxylene-ethoxylene, ethoxylene-1-propoxylene, butoxylene-n-propoxylene, pentadecyloxylene-methoxylene, and the like. When $M_1$ or $M_2$ is a branched or straight chain, dioxo-aliphatic group, preferably it has the formula —O—$(CH_2)_a$—O— or —O—$(CH_2)_a$—O—$(CH_2)_b$—, wherein each of a and b is from 1 to 7.

When either $M_1$ or $M_2$ is a branched or straight chain, carboxy-aliphatic group having from 1–20 carbon atoms, it can also be, for example, a divalent carboxylic acid ester such as the divalent radical of methyl formate, methyl acetate, ethyl acetate, n-propyl acetate, isopropyl acetate, n-butyl acetate, ethyl propionate, allyl propionate, t-butyl acrylate, n-butyl butyrate, vinyl chloroacetate, 2-methoxy-carbonylcyclohexanone, 2-acetoxycyclohexanone, and the like. When $M_1$ or $M_2$ is a branched or straight chain, carboxy-aliphatic group, it preferably has the formula —O—$CHR^2$—CO—O—$CHR^3$—, wherein $R^2$ and $R^3$ are each independently H, alkyl, alkoxy, aryl, aryloxy, heterocyclic or heterocycloxy.

When either $M_1$ or $M_2$ is a branched or straight chain, amino-aliphatic group having from 1–20 carbon atoms, it can be a divalent amine such as —$CH_2NH$—, —$(CH_2)_2N$—, —$CH_2(C_2H_5)N$—, —n—$C_4H_9NH$—, —t—$C_4H_9NH$—, —$CH_2(C_3H_7)N$—, —$C_2H_5(C_3H_7)N$—, —$CH_2(C_8H_{17})N$—, and the like. When $M_1$ or $M_2$ is a branched or straight chain, amino-aliphatic group, it preferably has the formula —$(CH_2)_a$—NR'— where R' is H or lower alkyl.

Preferably, $M_1$ and/or $M_2$ is an alkylene group having the formula —O—$(CH_2)_a$— where a is 1 to 7 and, most preferably, is a divalent ethylene group. In a particularly preferred embodiment, $M_1$ and $M_2$ are both present; $M_1$ and $M_2$ are not the same chemical entity; and $M_1$ and $M_2$ are n-pentylene and the divalent radical of methyl acetate respectively.

R in the polymer of the invention is H, alkyl, alkoxy, aryl, aryloxy, heterocyclic or heterocycloxy residue. Examples of useful alkyl R' groups include methyl, ethyl, n-propyl, i-propyl, n-butyl, tert-butyl, —$C_8H_{17}$, and the like groups; alkyl substituted with a non-interfering substituent, such as hydroxy, halogen, alkoxy or nitro; corresponding alkoxy groups; and alkyl conjugated to a biologically active substance to form a pendant drug delivery system.

When R is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When R is heterocyclic or heterocycloxy, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthyridine, pyrido[3,4-b]-pyridine, pyrido [3,2-b]-pyridine, pyrido[4,3-b]pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when R is heterocyclic or heterocycloxy, it is selected from the group consisting of furan, pyridine, N-alkylpyridine, 1,2,3- and 1,2,4-triazoles, indene, anthracene and purine rings.

In a particularly preferred embodiment, R is an alkyl group, an alkoxy group, a phenyl group, a phenoxy group, or a heterocycloxy group and, even more preferably, an alkoxy group having from 1 to 7 carbon atoms. Most preferably, R is an ethoxy group.

The molar ratio of n:(x or y) can vary greatly depending on the biodegradability and the release characteristics desired in the polymer, but typically varies between about 200:1 and 1:200. Preferably, the ratio x:y is from about 100:1 to about 1:100 and, most preferably, from about 50:1 to about 1:50.

The molar ratio of q:r can vary greatly depending on the biodegradability and the release characteristics desired in the polymer, but typically varies between about 1:200 and 200:1. Preferably, the ratio q:r is from about 1:150 to about 150:1 and, most preferably, from about 1:99 to about 99:1.

The molar ratio of x:y can also vary greatly depending on the biodegradability and the release characteristics desired in the polymer but, typically, is about 1.

Biodegradable polymers differ from non-biodegradable polymers in that they can be degraded during in vivo therapy. This generally involves breaking down the polymer into its monomeric subunits. In principle, the ultimate hydrolytic breakdown products of a poly(phosphoester) are phosphate, alcohol, and diol, all of which are potentially non-toxic. The intermediate oligomeric products of the hydrolysis may have different properties, but the toxicology of a biodegradable polymer intended for implantation or injection, even one synthesized from apparently innocuous monomeric structures, is typically determined after one or more in vitro toxicity analyses. A typical toxicity assay would be performed with live carcinoma cells, such as GT3TKB tumor cells, in the following manner:

About 100–150 mg of the sample polymer is degraded in 20 mL of 1M NaOH at 37° C. for 1–2 days, or until complete degradation is observed. The solution is then neutralized with 20 mL of 1M HCl. About 200 μL of various concentrations of the degraded polymer products are placed in 96-well tissue culture plates and seeded with human gastric carcinoma cells (GT3TKB) at $10^4$/well density. The degraded polymer products are incubated with the GT3TKB cells for 48 hours. The results of the assay can be plotted as % relative growth vs. concentration of degraded polymer in the tissue-culture well.

The biodegradable polymer of the invention is preferably sufficiently pure to be biocompatible itself and remains biocompatible upon biodegradation. By "biocompatible" is meant that the biodegradation products or the polymer itself are non-toxic and result in only minimal tissue irritation when implanted or injected into vasculated tissue.

The polymer of the invention is preferably soluble in one or more common organic solvents for ease of fabrication and processing. Common organic solvents include such solvents as chloroform, dichloromethane, acetone, ethyl acetate, DMAC, N-methyl pyrrolidone, dimethylformamide, and dimethylsulfoxide. The polymer is preferably soluble in at least one of the above solvents.

Synthesis of Poly(Phosphoester-co-ester) Polymers

The most common general reaction in preparing poly(phosphates) is a dehydrochlorination between a phosphorodichloridate and a diol according to the following equation:

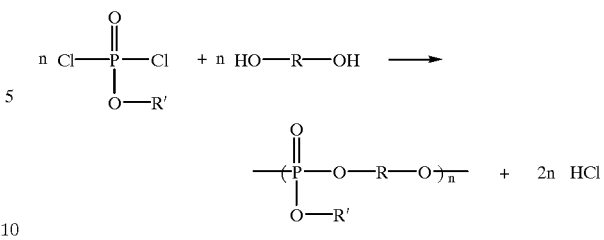

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as cross-linking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane. The solution polymerization must be run in the presence of equimolar amounts of the reactants and a stoichiometric amount of an acid acceptor, usually a tertiary amine such as pyridine or triethylamine. The product is then typically isolated from the solution by precipitation in a non-solvent and purified to remove the hydrochloride salt by conventional techniques known to those of ordinary skill in the art, such as by washing with an aqueous acidic solution, e.g., dilute HCl.

Reaction times tend to be longer with solution polymerization than with melt polymerization. However, because overall milder reaction conditions can be used, side reactions are minimized, and more sensitive functional groups can be incorporated into the polymer. The disadvantages of solution polymerization are that the attainment of high molecular weights, such as a Mw greater than 20,000, is less likely.

Interfacial polycondensation can be used when high molecular weight polymers are desired at high reaction rates. Mild conditions minimize side reactions. Also the dependence of high molecular weight on stoichiometric equivalence between diol and dichloridate inherent in solution methods is removed. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In a preferred embodiment of the invention, the biodegradable polymer of formula I or II is made by a process comprising the steps of:

(a) reacting at least one heterocyclic ring compound having formula III, IV or V:

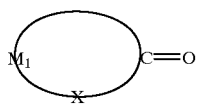

III

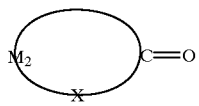

IV

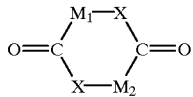

V wherein
$M_1$, $M_2$ and X are as defined above,
with an initiator having the formula:

H—Y—L—Y—H, wherein Y and L are as defined as above, to form a prepolymer of formula VI or VII, shown below:

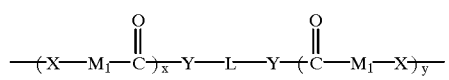

VI

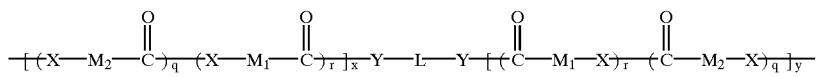

VII wherein X, $M_1$, $M_2$, Y, L, R, x, y, q and r are as defined above; and (b) further reacting said prepolymer of formula III, or IV or V with a phosphorodihalidate of formula VIII:

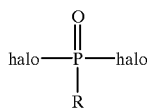

VIII where "halo" is Br, Cl or I; and R is as defined above, to form said polymer of formula I or II.

The function of the first reaction step (a) is to use the initiator to open the ring of the heterocyclic ring compound of formula III, IV or V. Examples of useful heterocyclic compounds of formula III, IV or V include caprolactones, caprolactams, amino acid anhydrides such as glycine anhydride, cycloalkylene carbonates, dioxanones, glycolids, lactides and the like.

When the compound of the invention has formula I, only one heterocyclic ring compound of formula III, which contains $M_1$, may be used to prepare the prepolymer of formula VI in step (a). When the compound of the invention has formula II, then a combination of a heterocyclic compound of formula III, which contains $M_1$, and a heterocyclic compound of formula IV, which contains $M_2$, may be used in step (a). Alternatively, when the compound of the invention has formula II, a single heterocyclic compound of formula V, which contains both $M_1$ and $M_2$, can be used in step (a).

Examples of suitable initiators include a wide variety of compounds having at least two active hydrogens (H—Y—L—Y—H) where L is a linking group and is defined above, and Y can be —O—, —S— or —NR", where R" is as defined above. The linking group L is can be a straight chain group, e.g., alkylene, but it may also be substituted with one or more additional active-hydrogen-containing groups. For example, L may a straight chain alkylene group substituted with one or more additional alkyl groups, each bearing a activated hydrogen moiety, such as —OH, —SH, or $NH_2$. In this way, various branched polymers can be prepared using the branched active hydrogen initiators to design the resulting polymer such that it has the desired properties. However, when branched polymers are reacted with acid chlorides, cross-linked polymers will result.

The reaction step (a) can take place at widely varying temperatures, depending upon the solvent used, the molecular weight desired, the susceptibility of the reactants to form side reactions, and the presence of a catalyst. Preferably, however, the reaction step (a) takes place at a temperature from about 0 to about +235° C. for melt conditions. Somewhat lower temperatures may be possible with the use of either a cationic or anionic catalyst.

The time required for the reaction step (a) also can vary widely, depending on the type of reaction being used and the molecular weight desired. Preferably, however, the reaction step (a) takes place during a time between about 1 hour and 7 days.

While the reaction step (a) may be in bulk, in solution, by interfacial polycondensation, or any other convenient method of polymerization, preferably, the reaction step (a) takes place under melt conditions.

Examples of particularly useful prepolymers of formula V include:

(i) OH-terminated prepolymer derived from polycaprolactone

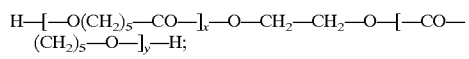

(ii) NH-terminated prepolymer derived from polycaprolactam (Nylon 6)

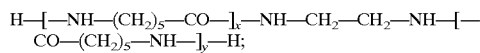

(iii) OH-terminated prepolymer derived from polylactide

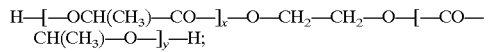

and (iv) OH-terminated prepolymer derived from polytrimethylene carbonate

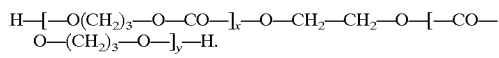

Examples of particularly useful prepolymers of formula VI include:

(i) OH-terminated copolymer derived from lactide and glycolide:

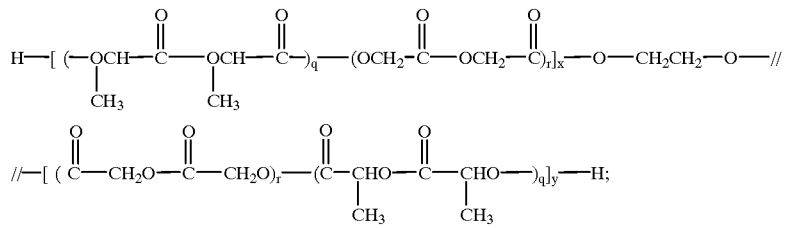

(ii) OH-terminated copolymer derived from lactide and caprolactone:

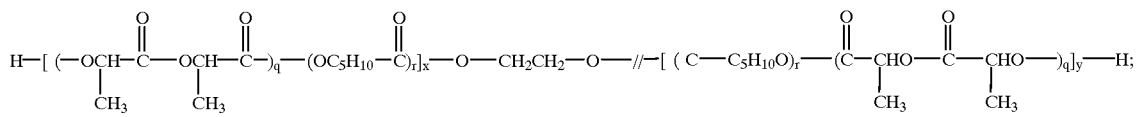

and (iii) OH-terminated copolymer derived from glycolide and caprolactone:

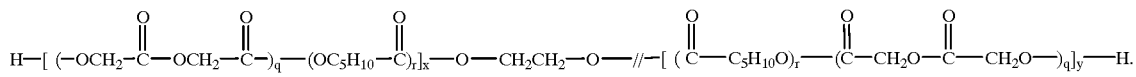

The purpose of the polymerization of step (b) is to form a polymer comprising (i) the prepolymer produced as a result of step (a) and (ii) interconnecting phosphorylated units. The result can be a block copolymer having a microcrystalline structure that is particularly well-suited to use as a controlled release medium.

The polymerization step (b) of the invention usually takes place at a slightly lower temperature than the temperature of step (a), but also may vary widely, depending upon the type of polymerization reaction used, the presence of one or more catalysts, the molecular weight desired, and the susceptibility of the reactants to undesirable side reaction. When melt conditions are used, the temperature may vary from about 0–150° C. However, when the polymerization step (b) is carried out in a solution polymerization reaction, it typically takes place at a temperature between about −40 and 100° C. Typical solvents include methylene chloride, chloroform, or any of a wide variety of inert organic solvents.

The time required for the polymerization of step (b) can also vary widely, depending on the molecular weight of the material desired and, in general, the need to use more or less rigorous conditions for the reaction to proceed to the desired degree of completion. Typically, however, the polymerization step (b) takes place during a time of about 30 minutes to 48 hours.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethyl-aminopyridine ("DMAP").

The polymers of formula I and II are isolated from the reaction mixture by conventional techniques, such as by precipitating out, extraction with an immiscible solvent, evaporation, filtration, crystallization and the like. Typically, however, the polymers of formulas I and II are both isolated and purified by quenching a solution of said polymer with a non-solvent or a partial solvent, such as diethyl ether or petroleum ether.

Biodegradability and Release Characteristics

The polymers of formulas I and II are usually characterized by a release rate of the biologically active substance in vivo that is controlled at least in part as a function of hydrolysis of the phosphoester bond of the polymer during biodegradation. Additionally, the biologically active substance to be released may be conjugated to the phosphorus sidechain R' to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

Accordingly, the structure of the sidechain can influence the release behavior of compositions comprising a biologically active substance. For example, it is expected that conversion of the phosphate sidechain to a more lipophilic, more hydrophobic or bulky group would slow down the degradation process. Thus, release is usually faster from polymer compositions with a small aliphatic group sidechain than with a bulky aromatic sidechain.

Polymer Compositions

The polymers of formulas I and II can be used either alone or as a composition containing, in addition, a biologically active substance to form a variety of useful biodegradable materials. For example, the polymers of formulas I and II can be used to produce a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable polymer composition comprises both:

(a) at least one biologically active substance and
(b) the polymer having the recurring monomeric units shown in formula I or II where X, $M_1$, $M_2$, L, R, Y, x, y, q, r and n are as defined above.

The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestyramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (1) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; and (n) anti-infective agents such as anti-fungals, anti-virals, antiseptics and antibiotics.

Preferably, the biologically active substance is selected from the group consisting of polysaccharides, growth factors, hormones, anti-angiogenesis factors, interferons or cytokines, and pro-drugs. More specifically, non-limiting examples of useful biologically active substances include the following therapeutic categories: analgesics, such as nonsteroidal anti-inflammatory drugs, opiate agonists and salicylates; antihistamines, such as $H_1$-blockers and $H_2$-blockers; anti-infective agents, such as antihelmintics, antianaerobics, antibiotics, aminoglycoside antibiotics, anti-fungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical anti-neoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, anti-emetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H₂-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuro-muscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, β-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful biologically active substances from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H₁-blocker antihistamines, such as clemastine and terfenadine; (5) H₂-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) β-blocker sympatholytics, such as atenolol; (35) adrenergic agonist sympathomimetics, such as albuterol and dobutamine; (36) cardiovascular agents, such as aspirin (ASA) (enteric coated ASA); (37) β-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propranolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as hydralazine and minoxidil; (52)

antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic anti-anemia agents, such as erythropoietin, filgrastim (G-CSF), and sargramostim (GM-CSF); (78) coagulation agents, such as antihemophilic factors 1–10 (AHF 1–10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin $B_{12}$) and niacin (vitamin $B_3$); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin.

Further, the following new drugs may also be used: recombinant beta-glucan; bovine immunoglobulin concentrate; bovine superoxide dismutase; the formulation comprising fluorouracil, epinephrine, and bovine collagen; recombinant hirudin (r-Hir, HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Still further, the following listing of peptides, proteins, and other large molecules may also be used, such as interleukins 1 through 18, including mutants and analogues; interferons α, β, and γ; luteinizing hormone releasing hormone (LHRH) and analogues, gonadotropin releasing hormone (GnRH), transforming growth factor-β (TGF-β); fibroblast growth factor (FGF); tumor necrosis factor-α& β (TNF-α& β); nerve growth factor (NGF); growth hormone releasing factor (GHRF); epidermal growth factor (EGF); fibroblast growth factor homologous factor (FGFHF); hepatocyte growth factor (HGF); insulin growth factor (IGF); invasion inhibiting factor-2 (IIF-2); bone morphogenetic proteins 1–7 (BMP 1–7); somatostatin; thymosin-α-1; γ-globulin; superoxide dismutase (SOD); and complement factors.

Alternatively, the biologically active substance may be a radiosensitizer, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); LlX (made by Terrapin); or the like.

In a particularly preferred embodiment, the biologically active substance is a therapeutic drug or pro-drug, most preferably a drug selected from the group consisting of chemotherapeutic agents and other anti-neoplastics, antibiotics, anti-virals, anti-fungals, anti-inflammatories, and anticoagulants. Most preferably, the biologically active substance is paclitaxel.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

Implants and Delivery Systems Designed for Injection

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body.

In a particularly preferred embodiment, an article is used for implantation, injection, or otherwise placed totally or partially within the body, the article comprising the biodegradable polymer composition of the invention. The biologically active substance of the composition and the polymer of the invention may form a homogeneous matrix, or the biologically active substance may be encapsulated in some way within the polymer For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is designed for implantation or injection into the body of an animal. It is particularly important that such an article result in minimal tissue irritation when implanted or injected into vasculated tissue.

As a structural medical device, the polymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable fabric, drug-carriers, biosorbable sutures, burn dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

Biodegradable medical implant devices and drug delivery products can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction.

Once a medical implant article is in place, it should remain in at least partial contact with a biological fluid, such as blood, internal organ secretions, mucous membranes, cerebrospinal fluid and the like.

EXAMPLES

Example 1

Synthesis of Poly(L-lactide-co-ethyl-phosphate) [Poly(LAEG-EOP)]

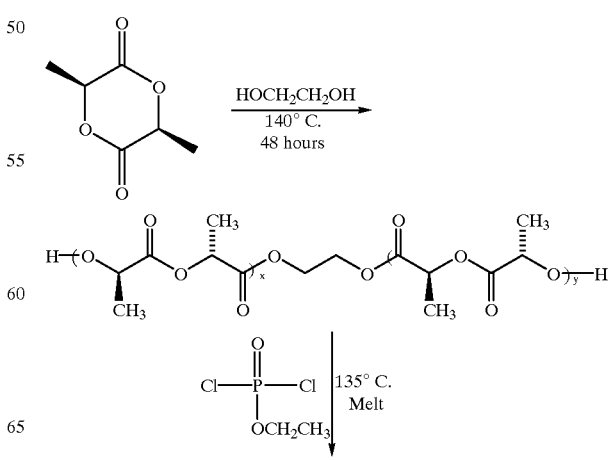

-continued

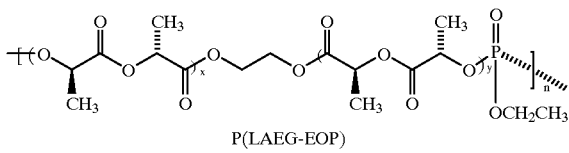

P(LAEG-EOP)

20 g (0.139 mole of (3S)-cis-3,6-dimethyl-1,4-dioane-2,5-dione (L-lactide) (obtained from Aldrich Chemical Company, recrystallized with ethyl acetate, sublimed, and recrystallized with ethyl acetate again) and 0.432 g (6.94 mmole) of ethylene glycol (99.8%, anhydrous, from Aldrich) were placed in a 250 mL round-bottomed flask flushed with dried argon. The flask was closed under vacuum and placed in an oven heated to 140° C. The flask was kept at this temperature for about 48 hours with occasional shaking.

The flask was then filled with dried argon and placed in oil bath heated to 135° C. Under an argon stream, 1.13 g of ethyl phosphorodichloridate was added with stirring. After one hour of stirring, a low vacuum (about 20 mm Hg) was applied to the system, and it was allowed to stand overnight. One hour before work-up, a high vacuum was applied. After cooling, the polymer was dissolved in 200 mL of chloroform and quenched into one liter of ether twice to an off-white precipitate, which was dried under vacuum.

Figure 6:
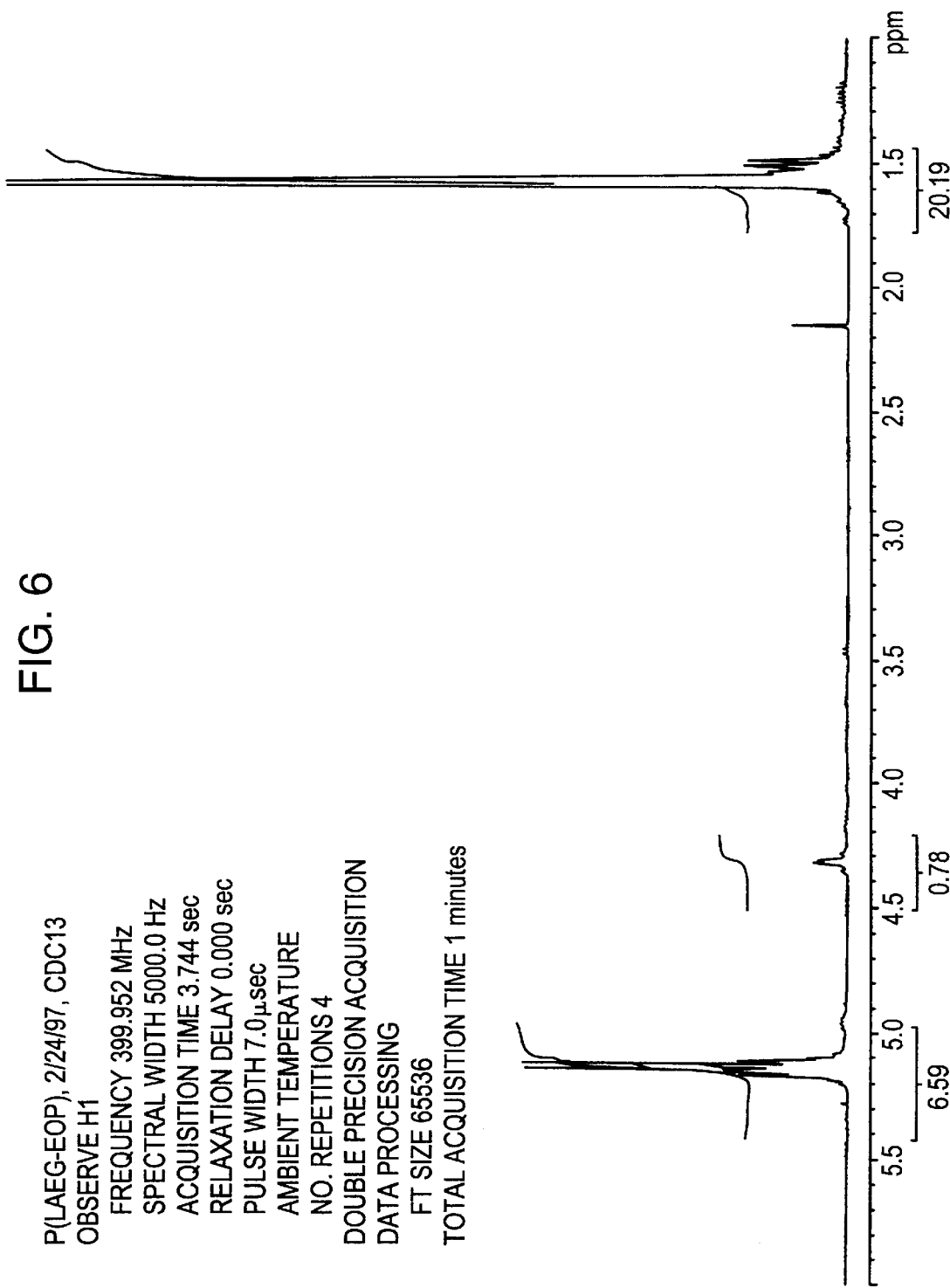
FIG. 6 shows the $^1$H-NMR spectrum of a polymer of the invention, P(LAEG-EOP).
Figure 7:
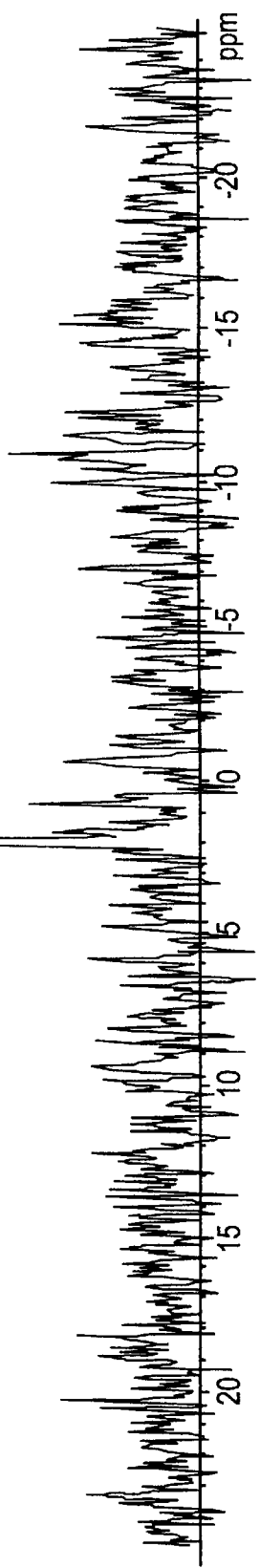
FIG. 7 shows the $^{31}$P-NMR spectrum of a polymer of the invention, P(LAEG-EOP).

It was confirmed by NMR spectroscopy that the polymer obtained was the desired product, poly(L-lactide-co-ethyl-phosphate) [p(LAEG-EOP)], as shown in FIGS. 6 and 7.

Example 2

ProDerties of P(LAEG-EOP)

A P(LAEG-EOP) polymer where (x or y)/n=10:1 was prepared as described above in Example 1. The resulting poly(phosphoester-co-ester) polymer was analyzed by GPC using polystyrene as a standard, and the resulting graph established an Mw of 33,000 and an Mn of 4800, as shown in FIG. 7.

Figure 2A:
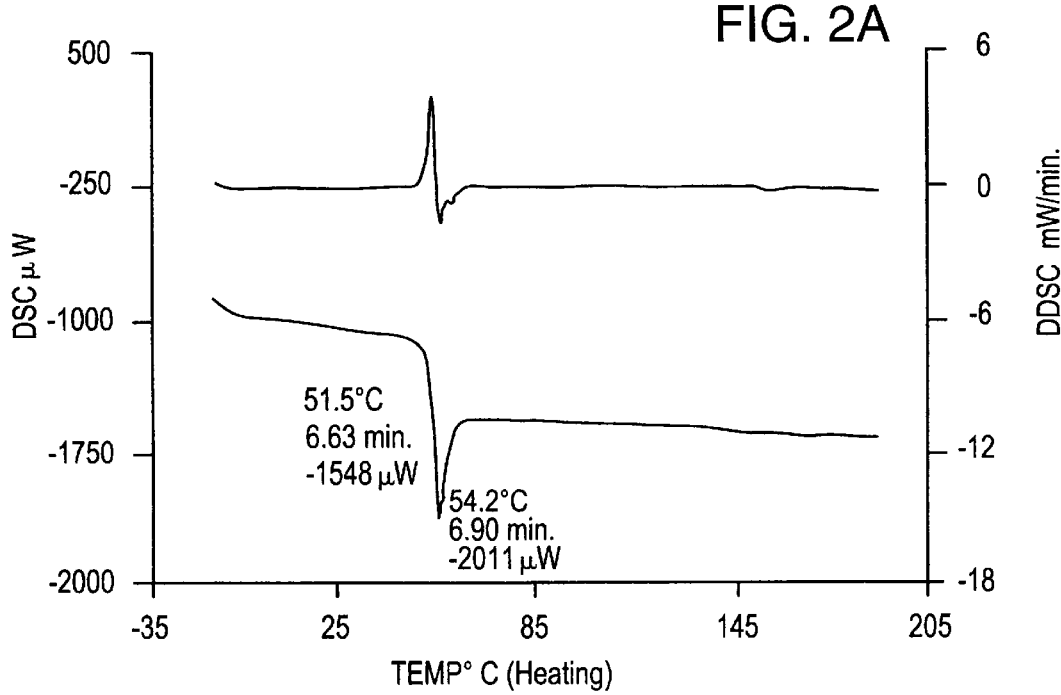
FIGS. 2A and 2B show differential scanning calorimetry data for two polymers of the invention.
Figure 2B:
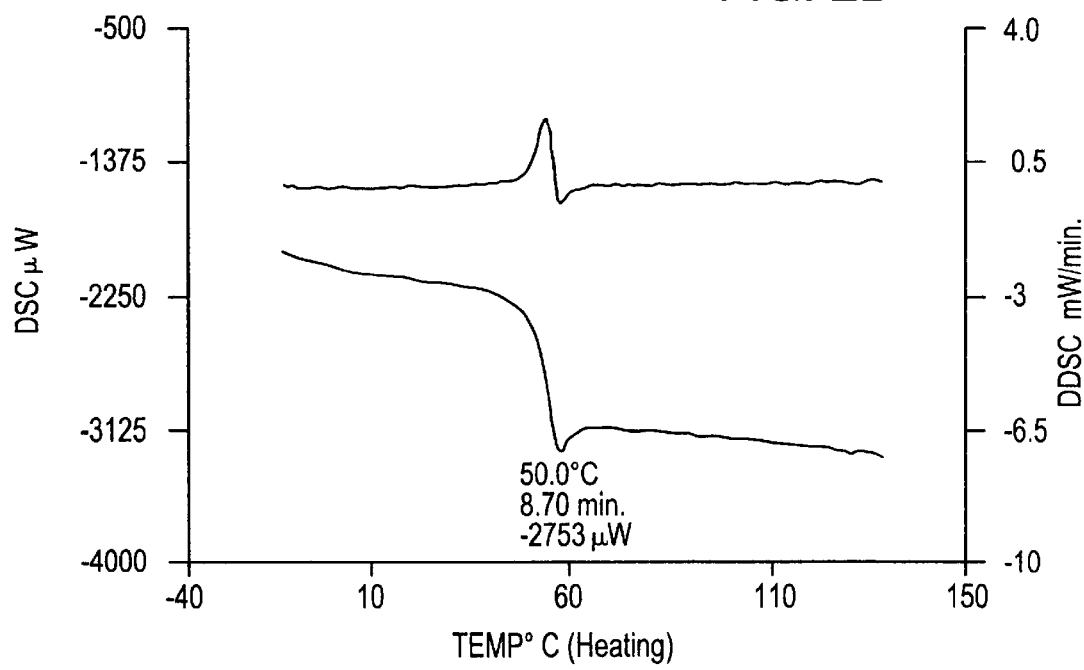

The viscosity was measured in chloroform ($CH_3Cl$) at 40° C. and determined to be 0.315 dL/g. The polymer was soluble in ethyl acetate, acetone, acetonitrile, chloroform, dichloromethane, tetrahydrofuran, N-methylpyrrolidone, dimethylformamide, and dimethyl sulfoxide. The polymer formed a brittle film, and the Tg was determined by DSC to be 51.5° C., as shown in FIGS. 2A and 2B.

Example 3

Synthesis of Poly(L-lactide-co-hexyl-phosphate) [Poly(LAEG-HOP)]

A second poly(L-lactide-phosphate) having the following structure:

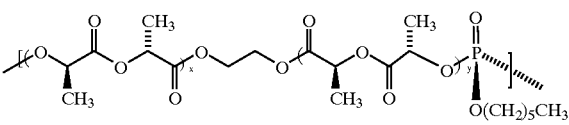

was also prepared by the method described in Example 1, except that hexyl phosphorodichloridate ("HOP") was substituted for EOP (ethyl phosphorodichloridate).

Example 4

Properties of P(LAEG-EOP) and P(LAEG-HOP)

Figure 5:
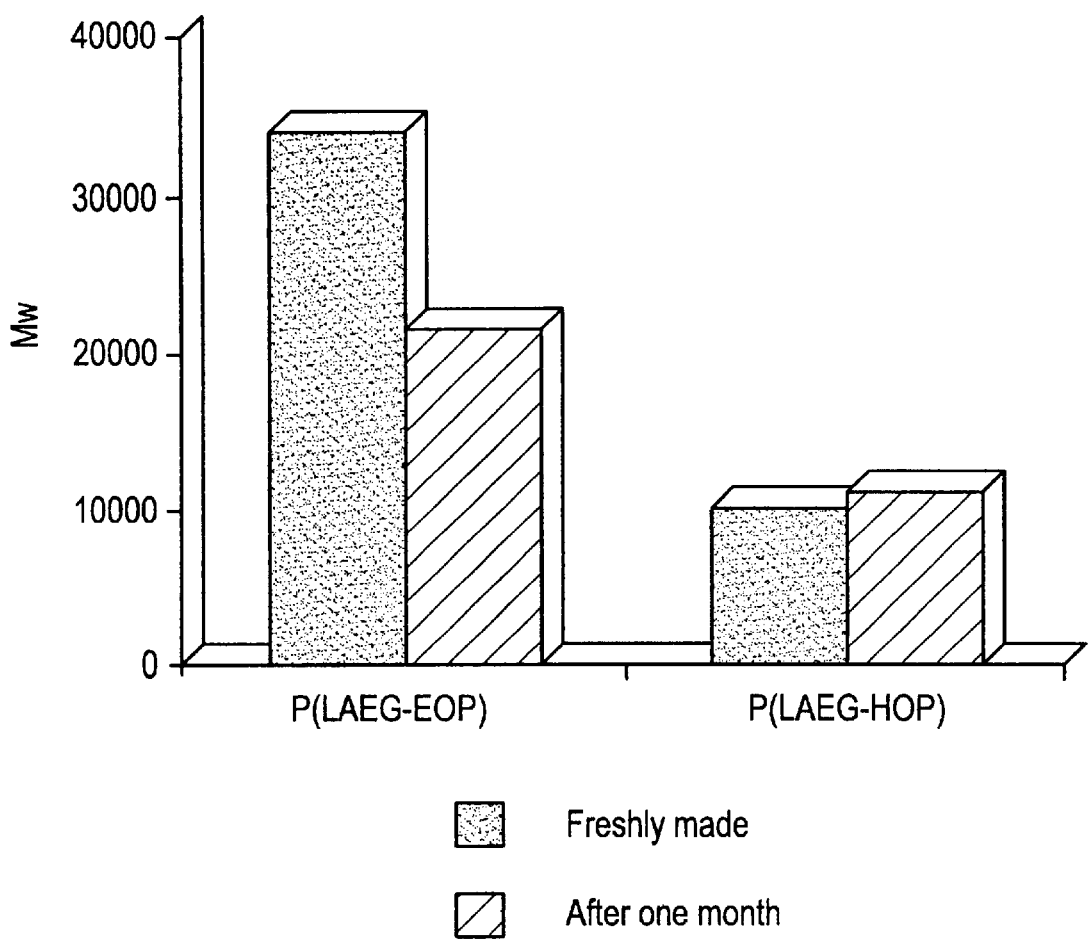
FIG. 5 shows the change in Mw of two polymers of the invention after being exposed to air at room temperature for one month.
Figure 8:
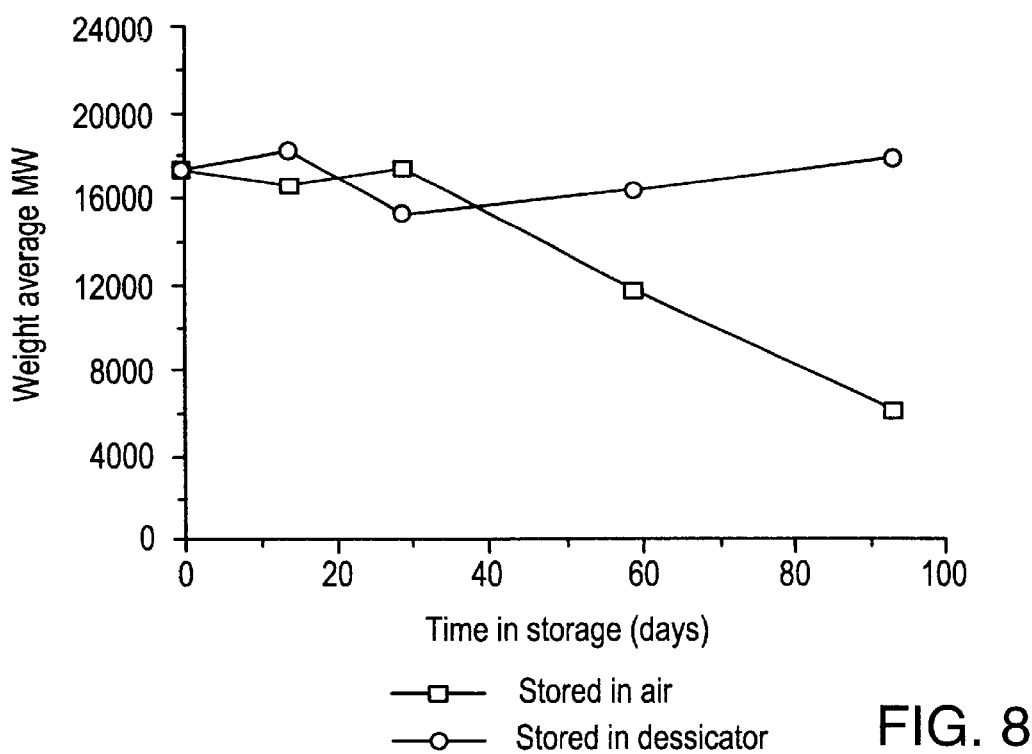
FIG. 8 shows shelf stability data for a polymer of the invention at room temperature.

The weight-average molecular weight (Mw) of the phosphoester-co-ester polymer of Example 1, P(LAEG-EOP), and the polymer of Example 3, P(LAEG-HOP), were first determined by gel permeation chromatography (GPC) with polystyrene as the calibration standard, as shown in FIG. 1. Samples of each were then allowed to remain exposed to room temperature air to test for ambient, unprotected storage capability. After one month, the Mw was again determined for each polymer. The results (plotted in FIG. 5) showed that, while the Mw for p(LAEG-EOP) was reduced by about one-third after a month of unprotected ambient conditions, the Mw for p(LAEG-HOP) remained fairly constant, even showing a slight increase. See also FIG. 8.

Discs for degradation studies were then fabricated from each polymer by compression molding at 50° C. and a pressure of 200 MPa. The discs were 4 mm in diameter, 1.5 mm in thickness, and 40 mg in weight. The degradation studies were conducted by placing the discs in 4 mL of 0.1M PBS (pH 7.4) at 37° C. Duplicate samples were removed at different time points up to eight days, washed with distilled water, and dried under vacuum overnight. Samples were analyzed for weight loss and molecular weight change (GPC), and the results are shown in FIGS. 4A, 4B, 10A and 11B. Both polymers, P(LAEG-EOP) and P(LAEG-HOP), demonstrated favorable degradation profiles.

Example 5

In vivo Biocompatibility of P(LAEG-EOP)

A 100 mg polymer wafer was formed from P(LAEG-EOP) and, as a reference, a copolymer of lactic and glycolic acid ["PLGA (RG755)"] known to be biocompatible. These wafers were inserted between muscle layers of the right limb of adult SPF Sprague-Dawley rats under anesthesia. The wafers were retrieved at specific times, and the surrounding tissues were prepared for histopathological analysis by a certified pathologist using the following scoring:

| Score | Level of Irritation |
|---|---|
| 0 | No Irritation |
| 0–200 | Slight Irritation |
| 200–400 | Mild Irritation |
| 400–600 | Moderate Irritation |
| More than 600 | Severe Irritation |

The results of the histopathological analysis are shown below in Table 8.

TABLE 8

| | Inflammatory Response at Site of Implantation (i.m.) | | | | | |
|---|---|---|---|---|---|---|
| Polymer | 3 Days | 7 Days | 14 Days | 1 Month | 2 Mos. | 3 Mos. |
| P(LAEG-EOP) | 130 | 123 | 180 | 198 | 106 | 99 |
| PLGA (RG755) | 148 | 98 | 137 | 105 | 94 | 43 |

See also FIG. 12. The phosphoester copolymer P(LAEG-EOP) was shown to have an acceptable biocompatability similar to that exhibited by the PLGA reference wafer.

Example 6

Preparation of Microspheres

Figure 3:
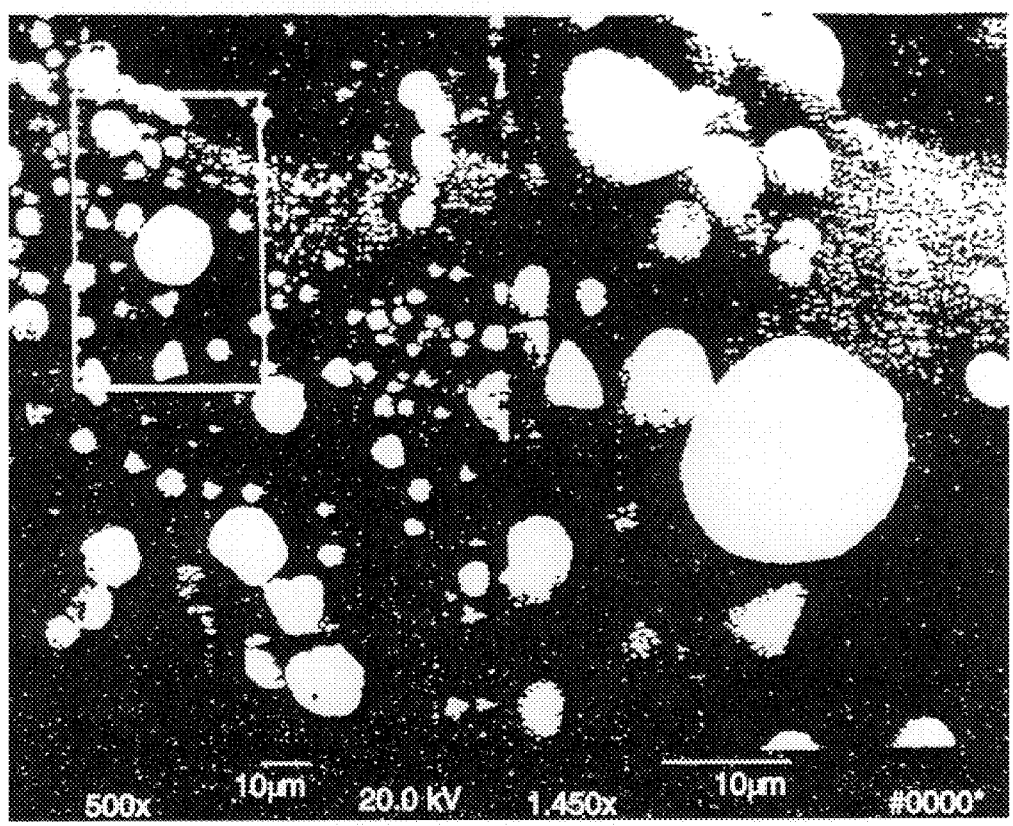
FIG. 3 shows the appearance of microspheres of a polymer of the invention made by the solvent evaporation method.
Figure 4A:
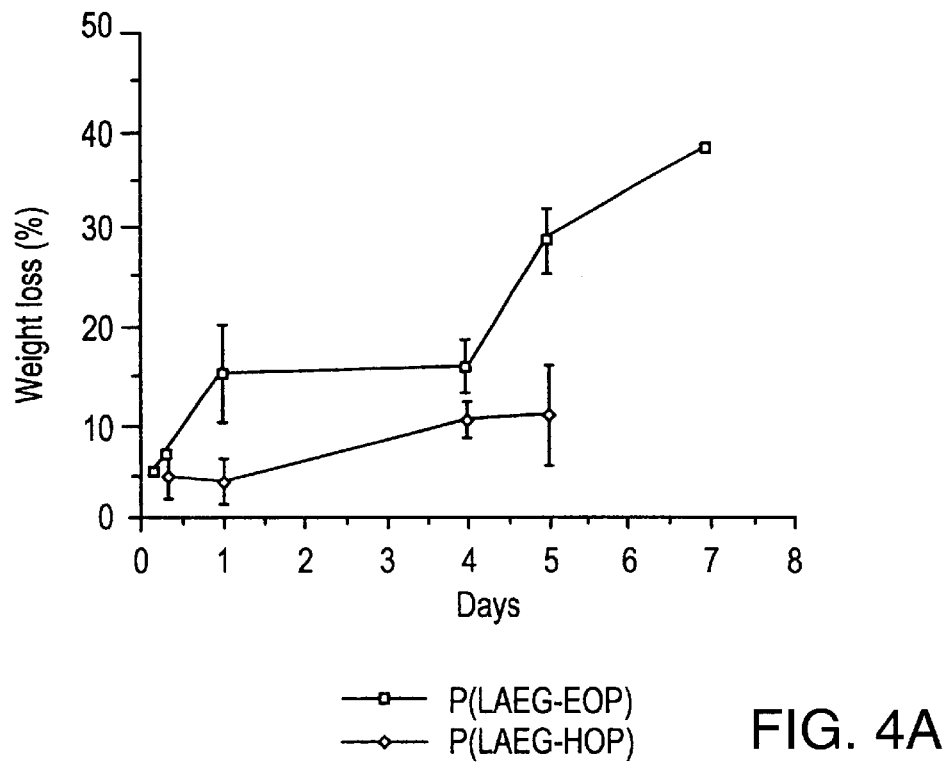
FIGS. 4A and 4B show the weight loss (4A) and the change in Mw (4B) for discs fabricated from two polymers of the invention over a period of eight days in PBS at 37° C.
Figure 4B:
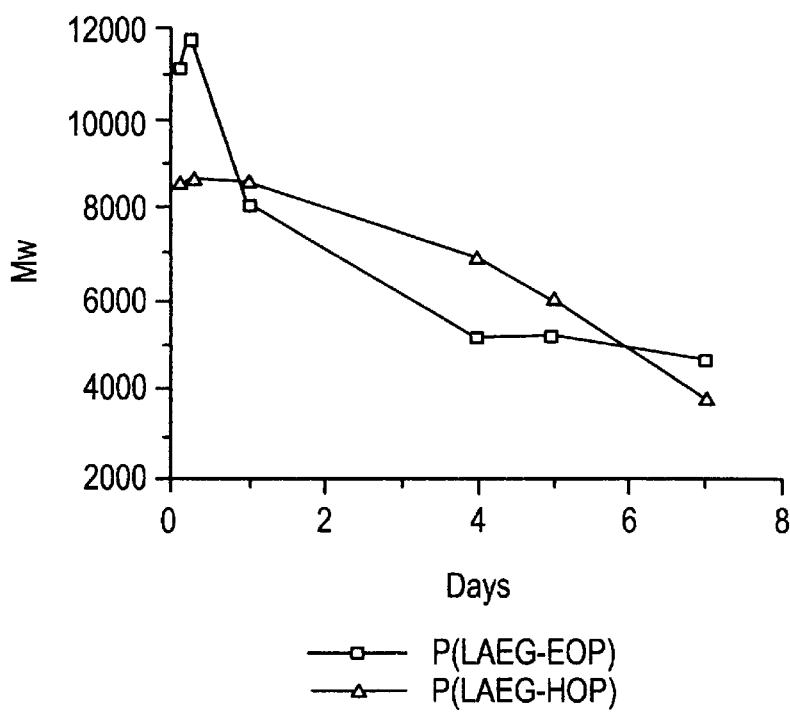

Microspheres were made from P(LAEG-EOP) by a solvent evaporation (double emulsion) method using methylene chloride as a solvent. The results are shown in FIG. 3.

Example 7

Preparation of Copolymer Microspheres Containing FITC-BSA with 10% Theoretical Loading Level One hundred mL of FITC-BSA solution (100 mg/mL dissolved in water) was added to a solution of 100 mg of P(LAEG-EOP) in 1 mL of methylene chloride, and emulsified via sonication for 15 seconds on ice. The resulting emulsion was immediately poured into 5 mL of vortexing a 1% solution of polyvinyl alcohol (PVA) in 5% NaCl, and vortexing was maintained for one minute. The emulsion thus formed was then poured into 20 mL of a 0.3% PVA solution in 5% NaCl, which was being stirred vigorously. Twenty five mL of a 2% solution of isopropanol was added, and the mixture was kept stirring for one hour to ensure complete extraction. The resulting microspheres were collected via centrifugation at 3000×g, washed 3 times with water, and freeze dried.

Different formulations of microspheres were made by using as the second aqueous phase a 5% NaCl solution or a 5% NaCl solution also containing 1% PEG 8000. Yet another technique was used in evaporating the solvent by stirring the mixture overnight, thus forming microspheres by solvent evaporation.

Example 8

Estimation of Encapsulation Efficiency and Loading Level

The loading level of FITC-BSA was determined by assaying for FITC after hydrolyzing the microspheres with 0.5 N NaOH overnight. The amount of FITC-BSA was compared with a standard curve that had been generated by making a series of FITC-BSA solutions in 0.5 N NaOH. The encapsulation efficiency of the microspheres was determined by comparing the quantity of FITC-BSA entrapped with the initial amount in solution via fluorometry. The encapsulation efficiency (%) and loading level (%) of FITC-BSA are shown in Table 1 below.

TABLE 1

Encapsulation Efficiency and Loading Level of FITC-BSA

|  | High Loading (24.98%) | Low Loading (1.5%) |
| --- | --- | --- |
| Loading (%) |  |  |
| Encapsulation Efficiency (%) | 98.10 | 91.70 |

Example 9

Cytotoxicity of the Copolymer

Figure 9:
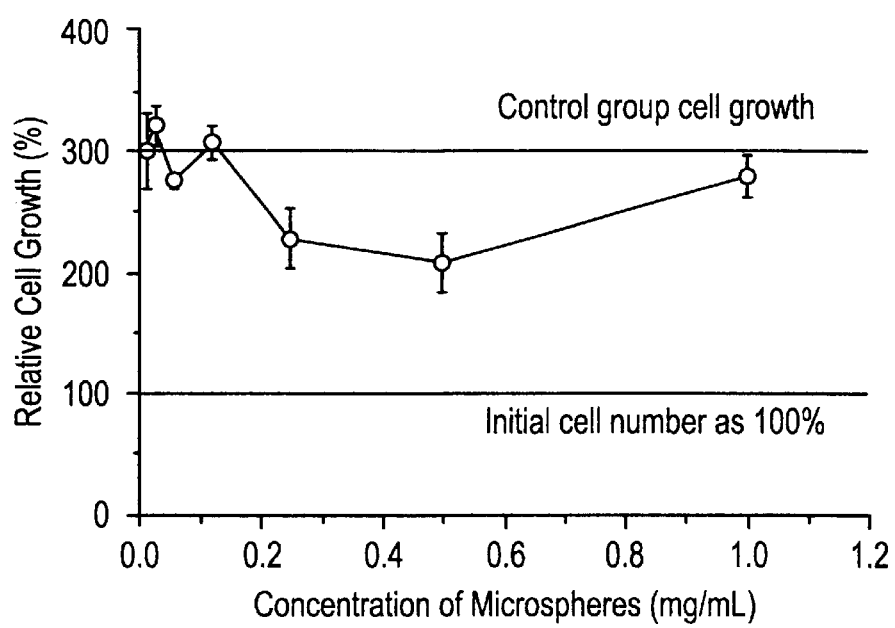
FIG. 9 shows cytotoxicity data for microspheres of a polymer of the invention, P(LAEG-EOP).
Figure 10A:
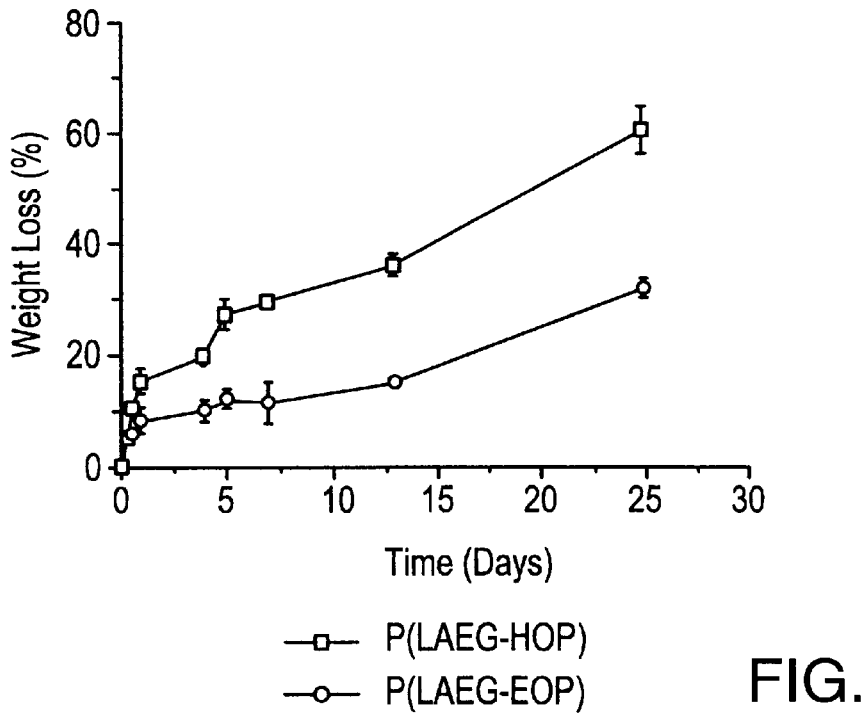
FIGS. 10A and 10B show the weight loss (10A) and the change in Mw (10B) for discs fabricated from two polymers of the invention, in vitro.
Figure 10B:
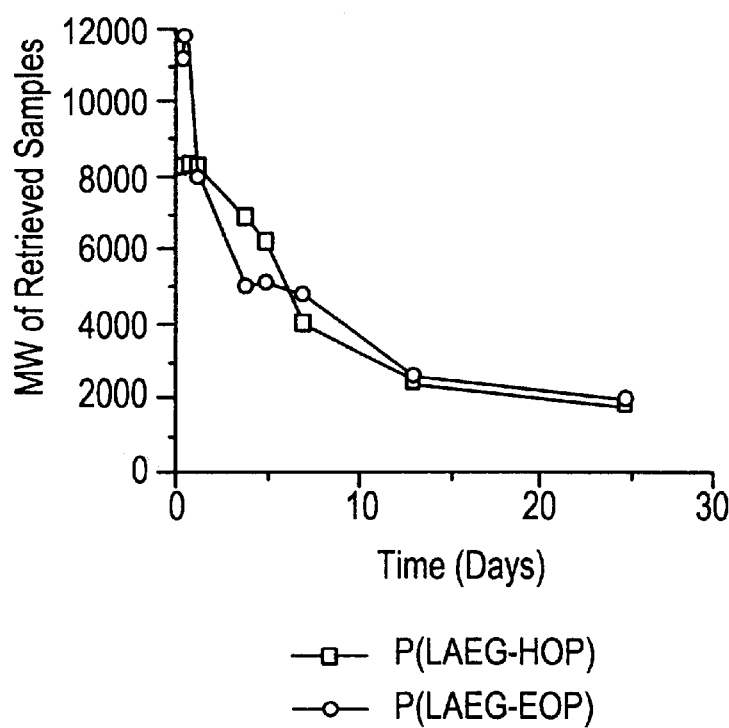
Figure 11A:
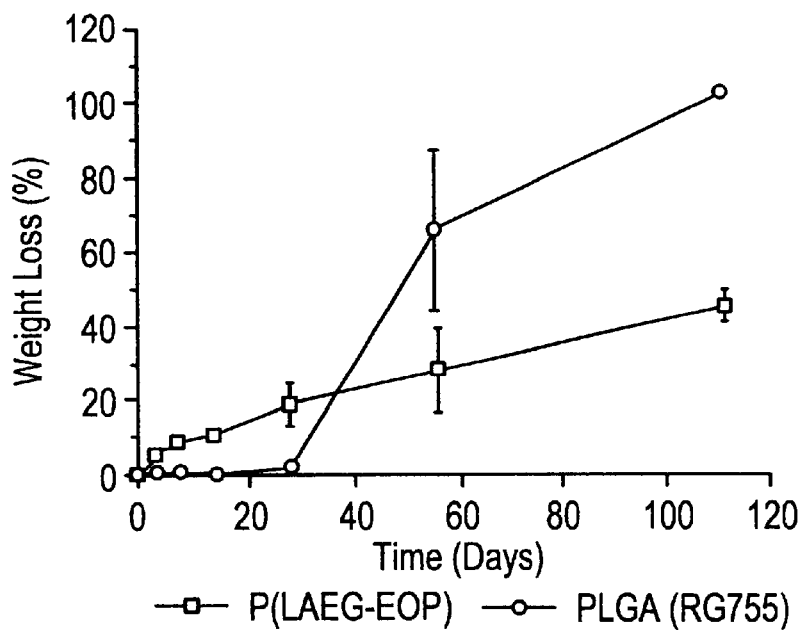
FIGS. 11A and 11B show the weight loss (11A) and the change in Mw (11B) for discs fabricated from the polymer of the invention, in vivo.
Figure 11B:
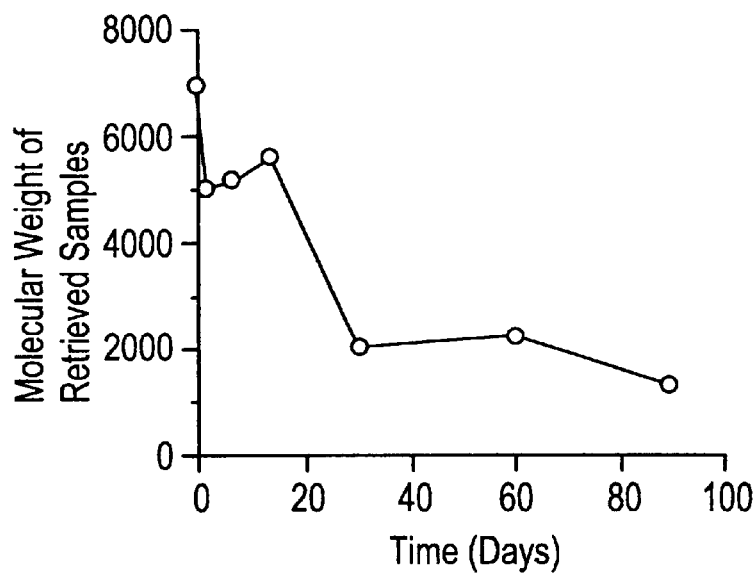

Microspheres containing P(LAEG-EOP) were added to 96-well tissue culture plates at different concentrations. Human gastric carcinoma cells (GT3TKB) were then seeded at a rate of $10^4$ cells/well. The cells were then incubated with the microspheres in the wells for 48 hours at 37° C. The cell proliferation rate was analyzed by MTT assay, and the results were plotted as % relative growth vs. concentration of copolymer microspheres in the tissue culture well, as shown in FIG. 9.

Example 10

Effect of Fabrication Method on the Release of FITC-BSA from Microspheres

Figure 13:
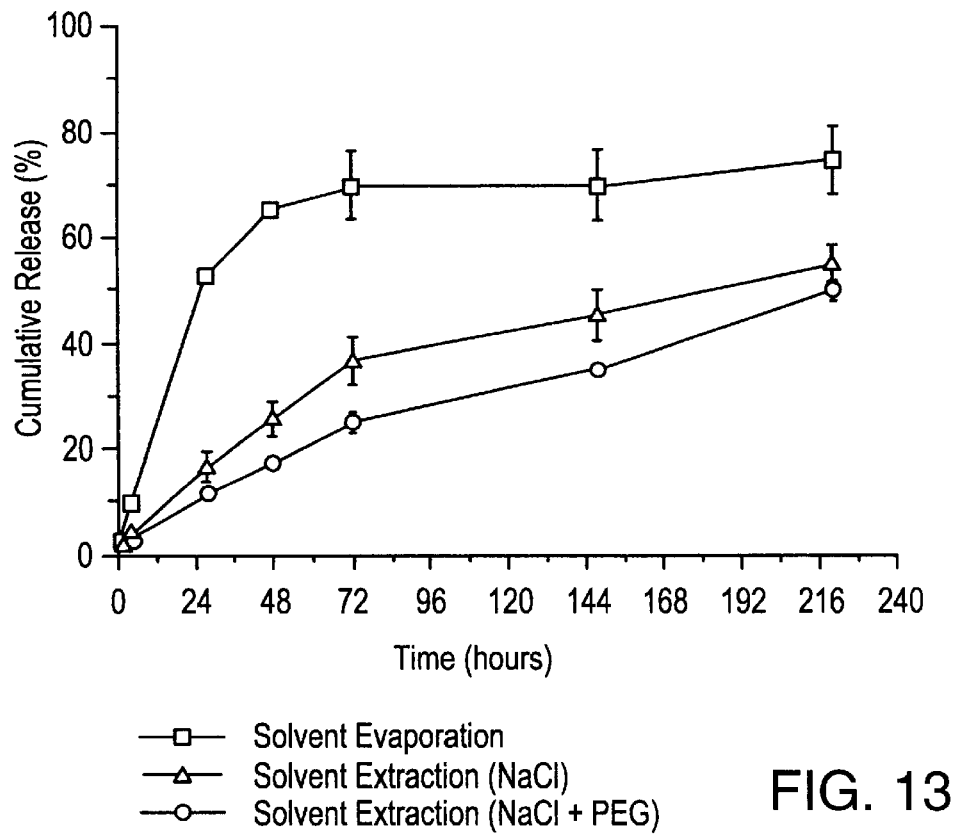
FIG. 13 shows the effect of fabrication method upon the release rate of microspheres of a polymer of the invention.
Figure 14:
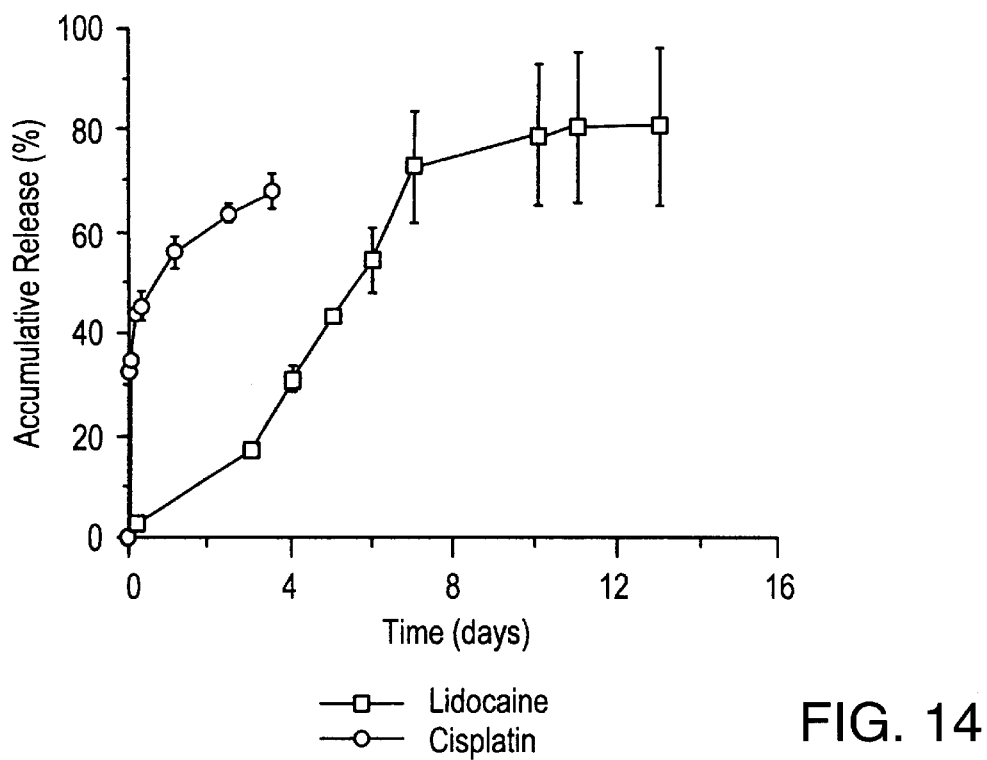
FIG. 14 shows the rate of release of lidocaine and cisplatin from microspheres of a polymer of the invention.
Figure 15:
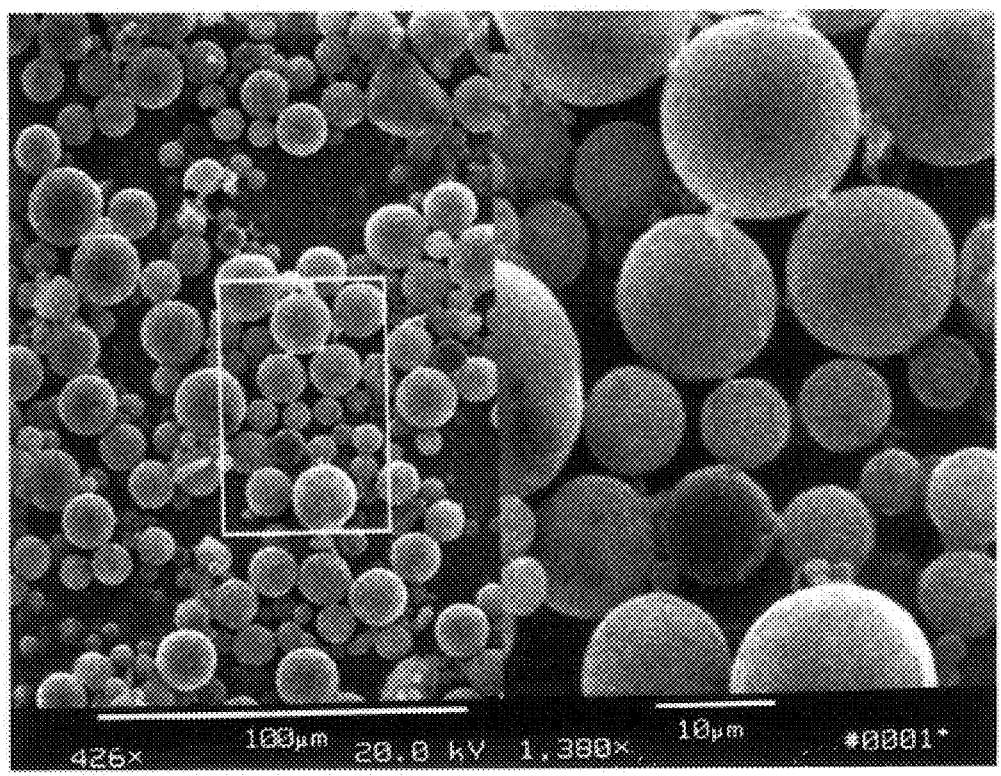
FIG. 15 shows the appearance of microspheres of a polymer of the invention containing FITC-BSA.

Fifty mg of microspheres of a polymer of the invention were suspended in vials containing 10 mL of PBS, and the vials were shaken in an incubator at 37° C. and at a rate of 220 rpm. The supernatant fluid was replaced at various time points, and the amount of FITC-BSA released was analyzed by spectrophotometry at 492 nm. The results were plotted as % cumulative release of FITC-BSA from the microspheres vs. time in hours, as shown in FIG. 13.

Example 11

Preparation of P(LAEG-EOP) Microspheres Containing Lidocaine Using Polyvinyl Alcohol as the Non-Solvent Phase A solution of 0.5% w/v polyvinyl alcohol (PVA) in deionized water solution was prepared in a 600 mL beaker by combining 1.05 g of PVA with 210 mL of deionized water. The solution was stirred for one hour and filtered. A polymer/drug solution was prepared by combining 630 mg of polymer and 70 mg of lidocaine in 7 mL of methylene chloride and mixing by vortex. The PVA solution was mixed at 500 rpm with an overhead mixer, and the polymer/drug solution was added dropwise. After 30 minutes of mixing, 200 mL of cold deionized water was added to the stirring PVA solution. The resulting mixture was stirred for a total of 3.5 hours. The microspheres formed were filtered off, washed with deionized water, and lyophilized overnight.

Figure 16:
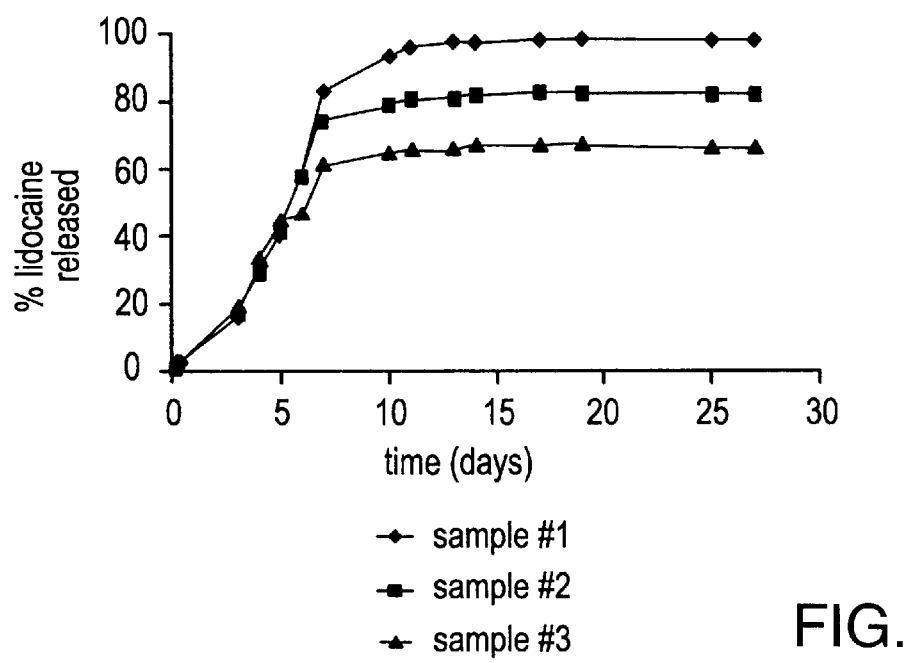
FIG. 16 shows the rate of release of lidocaine from microspheres of a polymer of the invention.

Microspheres loaded with 4.2% w/w lidocaine were thus obtained. Approximately 10 mg of microspheres were placed in a phosphate buffer saline (0.1M, pH 7.4) at 37° C. on a shaker and sampled regularly. The results were plotted as % lidocaine released vs. time in days, as shown in FIG. 16.

Example 12

Preparation of P(DAEG-EOP)

The d,l racemic mixture of poly(L-lactide-co-ethylphosphate) ["P(DAEG-EOP)"], was prepared in the same manner as P(LAEG-EOP), as described in Example 1.

Example 13

Preparation of P(DAEG-EOP) Microspheres with Lidocaine Using Silicon Oil as the Non-solvent Phase Two percent sorbitan-trioleate, which is commercially available from Aldrich under the tradename Span-85, in silicon oil was prepared in a 400 mL beaker by combining 3 mL of Span-85 with 150 mL of silicone oil and mixing with an overhead stirrer set at 500 rpm. A P(DAEG-EOP) polymer/drug solution was prepared by dissolving 400 mg of the polymer prepared above in Example 9, and 100 mg of lidocaine in 4.5 mL of methylene chloride. The resulting polymer/drug solution was added dropwise to the silicone oil/span mixture with stirring. The mixture was stirred for an hour and 15 minutes. The microspheres thus formed were filtered off and washed with petroleum ether to remove the silicone oil/span mixture, and lyophilized overnight.

Figure 17:
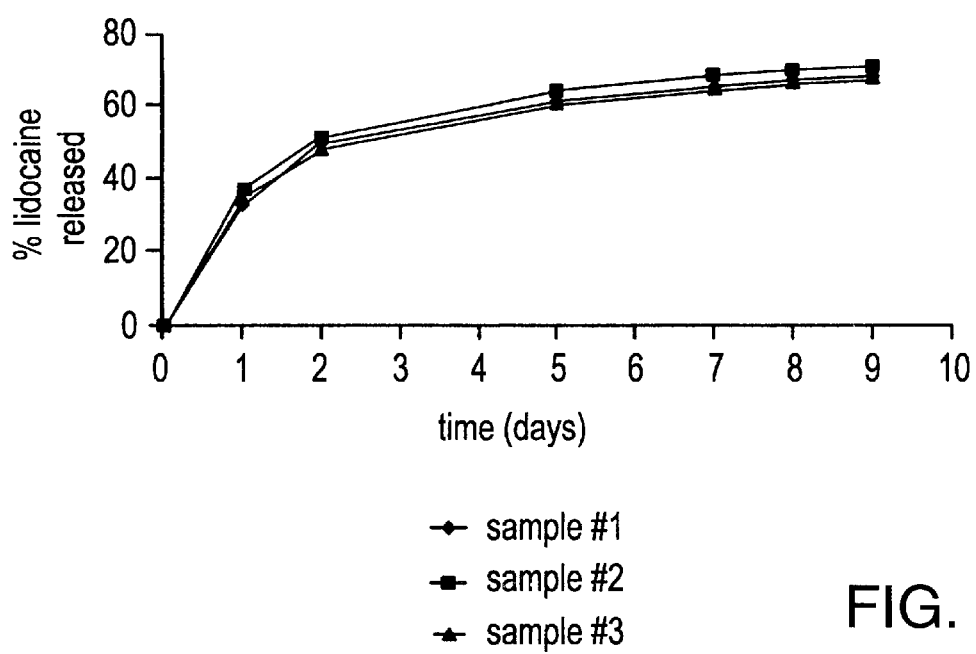
FIG. 17 shows the rate of release of lidocaine from microspheres of a polymer of the invention.

450 mg of microspheres loaded with 7.6% w/w lidocaine were thus obtained. Approximately 10 mg of microspheres were placed in phosphate buffer saline (0.1M, pH 7.4) at 37° C. on a shaker and sampled regularly. The results were plotted as % lidocaine released vs. time in days, as shown in FIG. 17.

Example 14

Biocompatibility of Poly(phosphoester) Microspheres in Mouse Peritoneal Cavity

The biocompatibility of biodegradable poly (phosphoester) microspheres of the invention was tested as follows:

Three 30 mg/mL samples of lyophilized poly(L-lactide-co-ethyl-phosphate) microspheres were prepared, the first having diameters greater than 75 microns, the second having diameters within the range of 75–125 microns, and the third having diameters within the range of 125–250 microns. Each sample was injected intra-peritoneally into a group of 18 female CD-1 mice having a starting body weight of 25 g. Animals in each group were weighed, sacrificed, and necropsied at 2, 7 and 14 days, and at 1, 2 and 3 months. Any lesions detected during the necropsy were graded on a scale of 0 to 4, with 0 indicating no response to treatment and 4 indicating a severe response to treatment.

Inflammatory lesions were observed to be restricted to an association with the microspheres on peritoneal surfaces or within fat tissue, and were compatible with foreign body isolation and encapsulation. Focal to multifocal supportive peritoneal steatitis with mesothelial hyperplasia was observed at 2–7 days, but gradually resolved by macrophage infiltration, the formation of inflammatory giant cells, and fibrous encapsulation of the microspheres at later sacrifices. Occasional adherence of microspheres to the liver and diaphragm, with associated inflammatory reaction, was also seen. Lesions related to microspheres were not seen within abdominal or thoracic organs. Microspheres, which were detected throughout the duration of the study, appeared transparent at early sacrifices but, at later times, developed crystalline material internally. effects on body growth were observed. The peritoneal reaction was observed to be limited to areas directly adjacent to the microspheres with no apparent deleterious effects on major thoracic or abdominal organs.

The invention being thus described, it will be obvious that the same may be varied in many ways. Such variations are not to be regarded as a departure from the spirit and scope of the invention and all such modifications are intended to be included within the scope of the following claims.

We claim:

1. A polymer composition, comprising a biodegradable polymer comprising the recurring monomeric units shown in formula I or II:

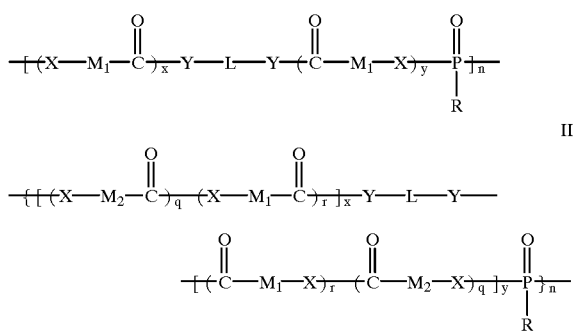

wherein:

X is —O—;

$M_1$ and $M_2$ are each independently (1) a —CH— group substituted with one aliphatic moiety having from 1–20 carbon atoms; or (2) a methylene group;

Y is —O—, —S— or —NR'—, wherein R' is H or alkyl;

L is a branched or straight chain aliphatic group having from 1–20 carbon atoms;

R is H, alkyl, alkoxy, aryl, aryloxy, heterocyclic or heterocycloxy;

the molar ratio of x:y is about 1;

the molar ratio n:(x or y) is between about 200:1 and 1:200; and the molar ratio q:r is between about 1:99 and 99:1;

wherein said biodegradable polymer is biocompatible before and upon biodegradation.

2. The polymer composition of claim 1, wherein each of $M_1$ and $M_2$ is a methyl-substituted —CH— group.

3. The polymer composition of claim 2, wherein the tertiary carbon atom of each said —CH— group for each occurrence of $M_1$ and $M_2$ in said monomeric unit may have a D or L configuration.

4. The polymer composition of claim 3, wherein the molar ratio n:(x or y) is between about 50:1 and 1:50.

5. The polymer composition of claim 3, wherein each of x and y is about 1 to 1,000.

6. The polymer composition of claim 3, wherein the molar ratio n:(x or y) is between about 100:1 and 1:100.

7. The polymer composition of claim 3, wherein said biodegradable polymer further comprises additional monomeric units.

8. The polymer composition of claim 3, wherein the amounts of said D and L configurations in said units are about the same.

9. The polymer composition of claim 2, wherein each of $M_1$ and $M_2$ is a methyl-substituted —CH— group; and L has from 1 to 7 carbon atoms.

10. The polymer composition of claim 9, wherein the tertiary carbon atom of each said —CH— group for each of $M_1$ and $M_2$ may have a D or L configuration.

11. The polymer composition of claim 10, wherein the amounts of said D and L configurations are about the same.

12. The polymer composition of claim 9, wherein each of $M_1$ and $M_2$ is a methyl-substituted —CH— group; L is a methyl-substituted ethylene group; and Y is —O—.

13. The polymer composition of claim 12, wherein each said —CH— group for each of $M_1$ and $M_2$ may have a D or L configuration for said tertiary carbon.

14. The polymer composition of claim 13, wherein the amounts of said D and L configurations are different.

15. The polymer composition of claim 12, wherein each of $M_1$ and $M_2$ is a methyl-substituted —CH— group; L is a methyl-substituted ethylene group; Y is —O—, and R is an alkoxy group.

16. The polymer composition of claim 15, wherein the tertiary carbon atom of each said —CH— group for each of $M_1$ and $M_2$ may have a D or L configuration.

17. The polymer composition of claim 16, wherein the amounts of said D and L configurations are about the same.

18. The polymer composition of claim 3, wherein said biodegradable polymer is biocompatible as determined by a toxicity analysis using GT3TKB cells and is biodegradable as determined by a degradation study using 0.1 M PBS.

19. The polymer composition of claim 2, wherein said polymer composition is in the form of microspheres.

20. The polymer composition of claim 1, wherein for each occurrence of $M_1$ and $M_2$ in said monomeric unit, $M_1$ and $M_2$ is optionally a methyl-substituted —CH— group or a methylene group.

21. The polymer composition of claim 20, wherein the molar ratio n:(x or y) is between about 50:1 and 1:50.

22. The polymer composition of claim 20, wherein the molar ratio q:r is between about 1:50 and 50:1.

23. The polymer composition of claim 20, wherein each of x and y is about 1 to 1,000.

24. The polymer composition of claim 20, wherein the molar ratio n:(x or y) is between about 100:1 and 1:100.

25. The polymer composition of claim 20, wherein said polymer composition comprises additional biocompatible monomeric units.

26. The polymer composition of claim 20, wherein said polymer composition is biocompatible as determined by an in vitro toxicity analysis and is biodegradable as determined by an in vitro degradation study.

27. The polymer composition of claim 20, wherein said polymer composition is in the form of microspheres.

28. The polymer composition of claim 20, wherein the amounts of said methyl substituted —CH— groups and said methylene groups are about the same.

29. The polymer composition of claim 28, wherein substantially all of said methyl-substituted —CH— groups are adjacent to at least one methylene group in said biodegradable polymer.

30. The polymer composition of claim 20, wherein the carbon atom for each said —CH— group for each occurrence of $M_1$ and $M_2$ in said monomeric unit may have a D or L configuration.

31. The polymer composition of claim 30, wherein the amounts of said D and L configurations are about the same.

32. The polymer composition of claim 20, wherein L has from 1 to 7 carbon atoms.

33. The polymer composition of claim 32, wherein Y is —O—.

34. The polymer composition of claim 33, wherein L is a methyl-substituted ethylene group.

35. The polymer composition of claim 34, wherein R is an alkoxy group.

36. The polymer composition of claim 20, wherein said polymer composition is in the form of microspheres.

37. The polymer composition of claim 30, wherein said biodegradable polymer is biocompatible as determined by a toxicity analysis using GT3TKB cells and is biodegradable as determined by a degradation study using 0.1 M PBS.

38. The polymer composition of claims 1, 3, 15, 20 or 30, further comprising a biologically active substance.

39. The polymer composition of claim 38, wherein said biologically active substance is a neoplastic agent.

40. The polymer composition of claim 39, wherein said neoplastic agent is paclitaxel.

41. The polymer of claims 1, 2, 13 or 30, further comprising a biologically active substance, wherein said biologically active substance is a local anesthetic.

42. The polymer composition of claim 41, wherein said local anesthetic is lidocaine.

43. The polymer composition of claims 1, 3, 13 or 21, further comprising a biologically active substance, wherein said biologically active substance is a radiosensitizer.

44. A polymer composition, comprising a biodegradable polymer comprising the recurring monomeric units shown in formula I or II:

$$\mathrm{I}$$

$$-\!\!\left[\!\left(X\!-\!M_1\!-\!\overset{O}{\overset{\|}{C}}\right)_{\!x}\!\!-\!\!Y\!-\!L\!-\!Y\!-\!\left(\overset{O}{\overset{\|}{C}}\!-\!M_1\!-\!X\right)_{\!y}\!\!-\!\overset{O}{\overset{\|}{\underset{R}{P}}}\right]_{\!n}\!-$$

-continued $$\mathrm{II}$$

$$-\!\!\left[\!\left[\!\left(X\!-\!M_2\!-\!\overset{O}{\overset{\|}{C}}\right)_{\!q}\!\!\left(X\!-\!M_1\!-\!\overset{O}{\overset{\|}{C}}\right)_{\!r}\right]_{\!x}\!\!-\!\!Y\!-\!L\!-\!Y\!-\right.$$
$$\left.\!\!\left[\!\left(\overset{O}{\overset{\|}{C}}\!-\!M_1\!-\!X\right)_{\!r}\!\!\left(\overset{O}{\overset{\|}{C}}\!-\!M_2\!-\!X\right)_{\!q}\right]_{\!y}\!\!-\!\overset{O}{\overset{\|}{\underset{R}{P}}}\right]_{\!n}\!-$$

wherein:

X is —O— or —NR'—, where R' is H or alkyl;

$M_1$ and $M_2$ are each independently (1) a branched or straight chain aliphatic group having from 1–20 carbon atoms; or (2) a branched or straight chain, oxy-, carboxy- or amino-aliphatic group having from 1–20 carbon atoms;

Y is —O—, —S— or —NR'—;

L is a branched or straight chain aliphatic group having from 1–20 carbon atoms;

R is H, alkyl, alkoxy, aryl, aryloxy, heterocyclic or heterocycloxy;

the molar ratio of x:y is about 1;

the molar ratio n:(x or y) is between about 200:1 and 1:200; and the molar ratio q:r is between about 1:99 and 99:1;

wherein said biodegradable polymer is biocompatible as determined by an in vitro toxicity analysis and is biodegradable as determined by an in vitro degradation study.

45. The polymer composition of claim 44, wherein each of $M_1$ and L is a branched or straight chain alkylene group.

46. The polymer composition of claim 44, wherein each of $M_1$ and L has from 1 to 7 carbon atoms.

47. The polymer composition of claim 44, wherein $M_1$ is a methylene group or a methyl-substituted —CH— group, and L is an ethylene group.

48. The polymer composition of claim 44, wherein R is an alkyl group, an alkoxy group, a phenyl group, a phenoxy group or a heterocycloxy group.

49. The polymer composition of claim 44, wherein R is an alkoxy group having from 1 to 7 carbon atoms.

50. The polymer composition of claim 44, wherein R is an ethoxy group.

51. The polymer composition of claim 44, wherein each of $M_1$ and $M_2$ is a branched or straight chain alkylene group.

52. The polymer composition of claim 44, wherein each of $M_1$ and $M_2$ has from 1 to 7 carbon atoms.

53. The polymer composition of claim 44, wherein X is —O—.

54. The polymer composition of claim 44, wherein $M_1$ and $M_2$ are each an alkylene or alkoxylene group; L is an alkylene group; and X is —O—.

55. The polymer composition of claim 44, wherein each of $M_1$ and $M_2$ is a methyl-substituted —CH— group.

56. The polymer composition of claim 53, wherein each of $M_1$ and $M_2$ is a methyl-substituted —CH— group; and L has from 1 to 7 carbon atoms.

57. The polymer composition of claim 53, wherein each of $M_1$ and $M_2$ is a methyl-substituted —CH— group; L is a methyl-substituted ethylene group; Y is —O—; and R is ethoxy.

58. The polymer composition of claim 54, wherein said methyl-substituted —CH— group for each of $M_1$ and $M_2$ may have a D or L configuration for said —CH— carbon atom.

59. The polymer composition of claim 58, wherein the amounts of said D and L configurations are about the same.

60. The polymer composition of claim 44, wherein for each occurrence of $M_1$ and $M_2$ in said monomeric unit, $M_1$ and $M_2$ is optionally a methyl-substituted —CH— group or a methylene group.

61. The polymer composition of claim 60, wherein the amounts of said methyl-substituted —CH— groups and said methylene groups are about the same.

62. The polymer composition of claim 61, wherein substantially all of said methyl-substituted —CH— groups are adjacent to at least one methylene group in said biodegradable polymer.

63. The polymer composition of claim 60, wherein the amounts of said methyl-substituted —CH— groups and said methylene groups are different.

64. The polymer composition of claim 60, wherein the tertiary carbon atom of each said methyl-substituted —CH— group for each occurrence of $M_1$ and $M_2$ in said monomeric unit may have a D or L configuration.

65. The polymer composition of claim 60, wherein the amounts of said D and L configurations are about the same in said monomeric units.

66. The polymer composition of claim 60, wherein L has from 1 to 7 carbon atoms.

67. The polymer composition of claim 60, wherein Y is —O—.

68. The polymer composition of claim 60, wherein L is a methyl-substituted ethylene group.

69. The polymer composition of claim 60, wherein R is an ethoxy group.

70. The polymer composition of claim 44, wherein the molar ratio n:(x or y) is between about 50:1 and 1:50.

71. The polymer composition of claim 44, wherein the molar ratio q:r is between about 1:50 and 50:1.

72. The polymer composition of claim 44, wherein each of x and y is about 1 to 1,000.

73. The polymer composition of claim 44, wherein the molar ratio n:(x or y) is between about 100:1 and 1:100.

74. The polymer composition of claims 44, 55 or 60, wherein said polymer composition is in the form of microspheres.

75. The polymer composition of claim 44, wherein said biodegradable polymer further comprises additional monomeric units.

76. The polymer composition of claims 44, 56 or 63, further comprising a biologically active substance.

77. The polymer composition of claim 76, wherein said biologically active substance is a neoplastic agent.

78. The polymer composition of claim 77, wherein said neoplastic agent is paclitaxel.

79. The polymer composition of claims 46, 55 or 60, further comprising a biologically active substance, wherein said biologically active substance is a local anesthetic.

80. The polymer composition of claim 79, wherein said local anesthetic is lidocaine.

81. The polymer composition of claims 44, 58 or 60, further comprising a biologically active substance, wherein said biologically active substance is a radiosensitizer.

82. A polymer composition comprising:

(a) at least one biologically active substance, and (b) a polymer having the recurring monomeric units shown in formula I or II:

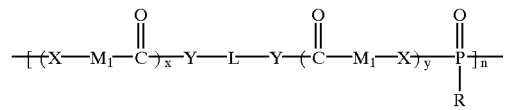

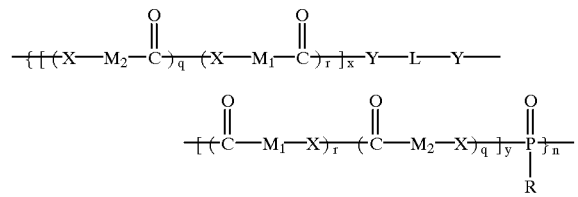

wherein:

X is —O— or —NR'—, where R' is H or alkyl;

$M_1$ and $M_2$ are each independently (1) a branched or straight chain aliphatic group having from 1–20 carbon atoms; or (2) a branched or straight chain, oxy-, carboxy- or amino-aliphatic group having from 1–20 carbon atoms;

Y is —O—, —S— or —NR'—;

L is a branched or straight chain aliphatic group having from 1–20 carbon atoms;

R is H, alkyl, alkoxy, aryl, aryloxy, heterocyclic or heterocycloxy;

the molar ratio of x:y is about 1;

the molar ratio n:(x or y) is between about 100:1 and 1:100; and the molar ratio q:r is between about 1:99 and 99:1.

83. The polymer composition of claim 82, wherein each of $M_1$ and L is a branched or straight chain alkylene group.

84. The polymer composition of claim 82, wherein R is an alkyl group, an alkoxy group, a phenyl group, a phenoxy group or a heterocycloxy group.

85. The polymer composition of claim 82, wherein R is an alkoxy group.

86. The polymer composition of claim 82, wherein each of $M_1$ and $M_2$ has from 1 to 7 carbon atoms.

87. The polymer composition of claim 82, wherein X is —O—.

88. The polymer composition of 82, wherein: $M_1$ and $M_2$ are each an alkylene or alkoxylene group; L is an alkylene group; X is —O—; and R is an alkoxy group.

89. The polymer composition of claim 82, wherein each of $M_1$ and $M_2$ is a methyl-substituted —CH— group.

90. The polymer composition of claim 89, wherein L has from 1 to about 7 carbon atoms.

91. The polymer composition of claim 89, wherein said methyl-substituted —CH— group for each of $M_1$ and $M_2$ may have a D or L configuration for said tertiary carbon.

92. The polymer composition of claim 91, wherein the amounts of said D and L configurations are the same.

93. The polymer composition of claim 82, wherein for each occurrence of $M_1$ and $M_2$ in said monomeric unit, $M_1$ and $M_2$ is optionally a methyl-substituted —CH— group or a methylene group.

94. The polymer composition of claim 93, wherein the amounts of said methyl-substituted —CH— groups and said methylene groups are about the same.

95. The polymer composition of claim 93, wherein substantially all of said methyl-substituted —CH— groups are adjacent to at least one methylene group in said polymer.

96. The polymer composition of claim 93, wherein the tertiary carbon atom of each said methyl-substituted —CH— group for each occurrence of $M_1$ and $M_2$ in said monomeric unit may have a D or L configuration.

97. The polymer composition of claim 96, wherein the amounts of said D and L configurations are about the same.

98. The polymer composition of claim 93, wherein L has from 1 to 7 carbon atoms.

99. The polymer composition of claim 82, wherein the molar ratio n:(x or y) is between about 50:1 and 1:50.

100. The polymer composition of claim 89, wherein the molar ratio q:r is between about 1:50 and 50:1.

101. The polymer composition of claim 93, wherein each of x and y is about 1 to 1,000.

102. The polymer composition of claim 82, wherein said polymer comprises additional biocompatible monomeric units.

103. The polymer composition of claims 82, 89 or 93, wherein said biologically active substance is a therapeutic drug or pro-drug.

104. The polymer composition of claim 103, wherein said drug is selected from the group consisting of anti-neoplastic agents, antibiotics, anti-virals, anti-fungals, anti-inflammatories, and anticoagulants.

105. The polymer composition of claims 82, 91 or 96, wherein said biologically active substance is a neoplastic agent.

106. The polymer composition of claim 105, wherein said neoplastic agent is paclitaxel.

107. The polymer composition of claims 82, 91 or 93, wherein said biologically active substance is an amide local anesthetic or an ester local anesthetic.

108. The polymer composition of claims 107, wherein said amide local anesthetic is lidocaine.

109. The polymer composition of claims 82, 91 or 96, wherein said biologically active substance is lidocaine.

110. The polymer composition of claims 82, 89 or 93, wherein said biologically active substance is a radiosensitizer.

111. The polymer composition of claim 26, wherein said in vitro toxicity analysis uses tumor cells.

112. The polymer composition of claim 111, wherein said in vitro toxicity analysis uses human carcinoma cells.

113. The polymer composition of claim 26, wherein said in vitro degradation study uses phosphate buffer saline.

114. The polymer composition of claim 15, wherein R is ethyloxy.

115. The polymer composition of claim 114, wherein the tertiary carbon atom of each said —CH— group for each of $M_1$ and M2 may have a D or L configuration.

116. The polymer composition of claim 115, wherein the amounts of said D or L configurations are about the same.

* * * * *